United States Patent
Palmer et al.

(10) Patent No.: US 11,510,707 B2
(45) Date of Patent: *Nov. 29, 2022

(54) ELASTIC MEMBER CLAMPS

(71) Applicant: GLOBUS MEDICAL, INC., Audubon, PA (US)

(72) Inventors: Rory Palmer, Spring City, PA (US); Basil Tharu, Philadelphia, PA (US); Aditya Muzumdar, King of Prussia, PA (US); Aditya Ingalhalikar, Pune (IN); Alexis Opp, West Chester, PA (US)

(73) Assignee: Globus Medical, Inc., Audubon, PA (US)

( * ) Notice: Subject to any disclaimer, the term of this patent is extended or adjusted under 35 U.S.C. 154(b) by 487 days.

This patent is subject to a terminal disclaimer.

(21) Appl. No.: 16/775,525

(22) Filed: Jan. 29, 2020

(65) Prior Publication Data
US 2020/0170683 A1    Jun. 4, 2020

Related U.S. Application Data

(63) Continuation of application No. 16/018,368, filed on Jun. 26, 2018, now Pat. No. 10,575,879, which is a continuation of application No. 15/044,251, filed on Feb. 16, 2016, now Pat. No. 10,034,692, which is a continuation-in-part of application No. 14/053,281, (Continued)

(51) Int. Cl.
*A61B 17/70* (2006.01)
*A61B 17/88* (2006.01)

(52) U.S. Cl.
CPC ...... *A61B 17/7053* (2013.01); *A61B 17/7041* (2013.01); *A61B 17/7086* (2013.01); *A61B 17/8869* (2013.01)

(58) Field of Classification Search
CPC ............ A61B 17/7056; A61B 17/7053; A61B 17/8869
See application file for complete search history.

(56) References Cited

U.S. PATENT DOCUMENTS 3,507,270 A    4/1970  Ferrier
5,788,697 A    8/1998  Kilpela et al.
(Continued)

FOREIGN PATENT DOCUMENTS

EP    2047813 A1    4/2009
JP    8505304 A     6/1996
(Continued)

*Primary Examiner* — Jan Christopher L Merene

(57) ABSTRACT

The present application generally relates to orthopedic stabilization systems, and in particular, to systems including clamps. The clamps can be used in addition to or to replace hooks that grasp onto bone members, such as the lamina. One example of such a clamp is an in-line clamp that includes a central opening for receiving a rod member, a first opening for receiving a set screw and a second opening for receiving an elastic member therethrough. Another example of such a clamp is an off-set clamp that includes an upper plate, a bottom plate, and an opening for receiving a rod therein. The upper plate can be separated from the bottom plate to make space for an elastic member that can be secured within the plates. Tulip clamps that utilize one or more elastic members are also provided.

18 Claims, 22 Drawing Sheets

Related U.S. Application Data filed on Oct. 14, 2013, now Pat. No. 9,433,441, which is a continuation-in-part of application No. 13/785,487, filed on Mar. 5, 2013, now Pat. No. 10,548,644.

(56) References Cited

U.S. PATENT DOCUMENTS

| | | | |
|---|---|---|---|
| 6,443,955 B1 * | 9/2002 | Ahrend | A61B 17/8866 606/103 |
| 6,482,208 B1 | 11/2002 | Ahrend et al. | |
| 6,689,140 B2 | 2/2004 | Cohen | |
| 8,162,946 B2 | 4/2012 | Baccelli et al. | |
| 8,257,367 B2 | 9/2012 | Bryant et al. | |
| 8,323,318 B2 | 12/2012 | Baccelli et al. | |
| 8,469,966 B2 | 6/2013 | Allen et al. | |
| 8,728,083 B2 | 5/2014 | Baccelli et al. | |
| 8,814,910 B2 | 8/2014 | Baccelli et al. | |
| 9,204,902 B2 | 12/2015 | Belliard et al. | |
| 9,204,903 B2 | 12/2015 | Belliard et al. | |
| 9,675,386 B2 * | 6/2017 | Akbarnia | A61B 17/8869 |
| 2012/0130373 A1 * | 5/2012 | Larroque-Lahitette | A61B 17/842 606/74 |
| 2012/0271354 A1 * | 10/2012 | Baccelli | A61B 17/7053 606/279 |
| 2013/0261680 A1 * | 10/2013 | Baccelli | A61B 17/8869 606/86 A |
| 2014/0257397 A1 * | 9/2014 | Akbarnia | A61B 17/7053 606/279 |
| 2016/0262806 A1 * | 9/2016 | Hsu | A61B 17/7076 |
| 2018/0021077 A1 * | 1/2018 | Simpson | A61B 17/7034 606/279 |

FOREIGN PATENT DOCUMENTS

| | | |
|---|---|---|
| JP | 2004512899 A | 4/2004 |
| JP | 2010000352 A | 1/2010 |
| JP | 2011500120 A | 1/2011 |
| WO | 0238063 A2 | 5/2002 |
| WO | 2012176096 A1 | 12/2012 |

* cited by examiner

US 11,510,707 B2

ELASTIC MEMBER CLAMPS

REFERENCE TO RELATED APPLICATIONS

The present application is a continuation of U.S. patent application Ser. No. 16/018,368, filed on Jun. 26, 2018 (published as U.S. Pat. Pub. No. 2018-0296251), which is a continuation of U.S. patent application Ser. No. 15/044,251, filed Feb. 16, 2016 (now U.S. Pat. No. 10,034,692), which is a continuation-in-part application of U.S. patent application Ser. No. 14/053,281, filed Oct. 14, 2013 (now U.S. Pat. No. 9,433,441), which is a continuation-in-part application of U.S. patent application Ser. No. 13/785,487, filed Mar. 5, 2013 (published as U.S. Pat. Pub. No. 2014-0257400). Each of these applications is hereby incorporated-by-reference in its entirety for all purposes.

FIELD OF THE INVENTION

The present application is generally directed to orthopedic stabilization systems, and in particular, to systems including clamps and rod members.

BACKGROUND

Many types of spinal irregularities cause pain, limit range of motion, or injure the nervous system within the spinal column. These irregularities can result from, without limitations, trauma, tumor, disc degeneration, and disease. Often, these irregularities are treated by immobilizing a portion of the spine. This treatment typically involves affixing a plurality of screws, hooks and/or clamps to one or more vertebrae and connecting the screws, hooks and/or clamps to an elongate rod that stabilizes members of the spine.

Accordingly, there is a need for improved systems involving screws, hooks and/or clamps for spinal stabilization.

SUMMARY OF THE INVENTION

Various systems, devices and methods related to spinal clamps are provided. In some embodiments, a spinal system comprises a clamp for receiving an elongate rod therein, wherein the clamp comprises an inner opening for receiving the elongate rod, a first opening in communication with the inner opening, and a second opening in communication with the inner opening; a set screw received in the first opening of the clamp; a bushing positioned at a distal end of the set screw; and an elastic member received in the second opening of the clamp, wherein the elastic member is configured to be in contact with the elongate rod received in the clamp.

In other embodiments, a spinal system comprises a clamp for receiving an elongate rod therein, wherein the clamp comprises an inner opening for receiving the elongate rod, a first opening in communication with the inner opening, and a second opening in communication with the inner opening, wherein the inner opening includes a groove for receiving an elastic member therein; a set screw received in the first opening of the clamp; and an elastic member received in the second opening of the clamp, wherein the elastic member is configured to be in contact with the elongate rod received in the clamp.

In other embodiments, a spinal system comprises a clamp for receiving an elongate rod therein, wherein the clamp comprises an inner opening for receiving the elongate rod, a first opening in communication with the inner opening, and a second opening in communication with the inner opening; a set screw received in the first opening of the clamp; a bushing in contact with a distal end of the set screw, wherein the set screw includes a protrusion that extends past a portion of the bushing; and an elastic member received in the second opening of the clamp, wherein the elastic member is configured to be in contact with the elongate rod received in the clamp.

DETAILED DESCRIPTION OF THE ILLUSTRATED EMBODIMENTS

The present disclosure relates to spinal stabilization devices, and in particular, clamps that utilize elastic members to grasp onto bone. The various clamps can be placed in many positions relative to a bone member, such as in-line or off-set.

Many spinal components exist to assist in stabilizing spinal members. Among the components that are used are spinal hooks, which can grasp onto bone. While spinal hooks are effective and can be less disruptive and prone to causing injury compared to other components, such as screws, there is a possibility of the hooks disengaging post surgery, therefore leading to potentially additional surgical intervention to rectify.

The present application is directed to spinal stabilization devices that overcome challenges associated with current spinal devices. In particular, it has been found that spinal clamps can be effectively provided that use elastic members, such as elastic bands, to grasp onto bone members. The use of the elastic members advantageously secures the clamps to bone, and reduces the risk of the devices being inadvertently removed from the bone post-surgery.

Figure 1A:
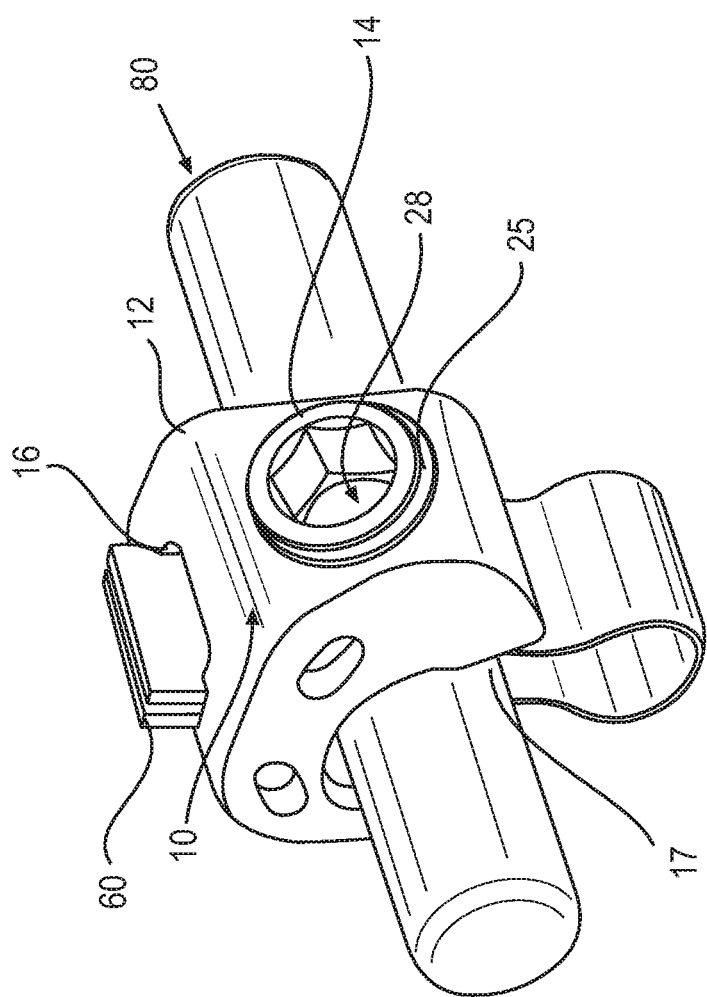
FIG. 1A is a top perspective view of an in-line clamp according to some embodiments.
Figure 1B:
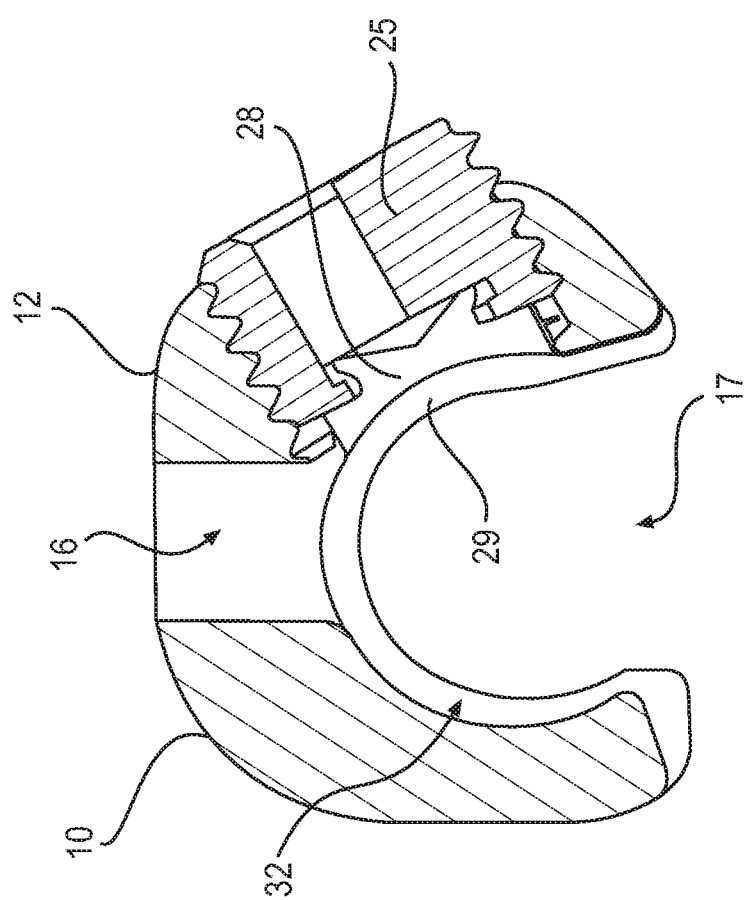
FIG. 1B is a side cross-sectional view of the in-line clamp in FIG. 1A.

FIGS. 1A-1C illustrate different views of an in-line clamp utilizing an elastic member, according to some embodiments. The in-line clamp 10 comprises a body 12 for receiving a rod member 80 therein. The in-line clamp 10 is configured to receive an elastic member 60 therethrough to secure the clamp 10 to a bone member (e.g., a vertebral body).

Figure 2A:
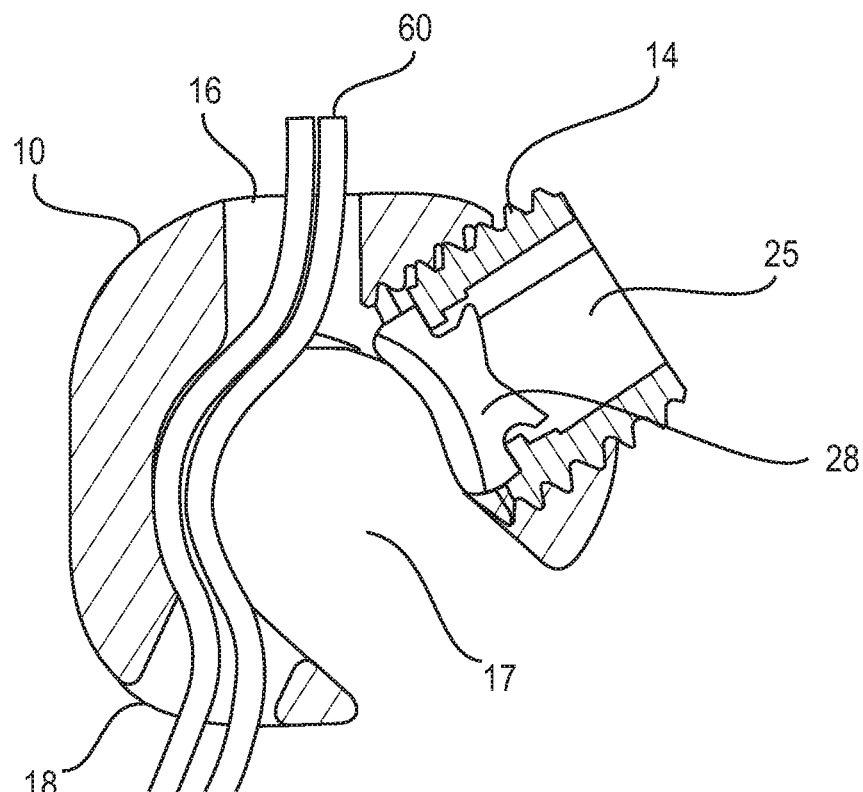
FIG. 2A is a side cross-sectional view of an alternative in-line clamp according to some embodiments.

The in-line clamp 10 includes a body 12 that forms a curved opening or mouth 17 for receiving a rod member 80 therein. As shown in FIG. 1A, in some embodiments, the curved opening 17 of the body 12 is formed facing downwardly over the rod member 80, such that the rod member 80 is bottom-loaded relative to the clamp 10. Advantageously, the curved opening 17 is also configured to receive a portion of the elastic member 60, which wraps around a vertebral body or bone member. As shown in FIG. 1A, the elastic member 60 can be positioned such that a first portion of the elastic member 60 is in contact with a first side of the rod member 80 and a second portion of the elastic member 60 is in contact with a second side of the rod member 80 opposite from the first side after looping the elastic member around a bone member. In other embodiments, such as shown in FIG. 2A, the elastic member 60 can be configured such that portions of the elastic member 60 remain pressed between one-side of the rod member 80 and an inner wall of the clamp 10, even after looping the elastic member 60 around a bone member. One skilled in the art will appreciate that the positioning of the elastic member 60 relative to the rod member 80 and the clamp 10 can vary, and that the illustrations shown herein are not meant to limit the positions available for placing the elastic member, but rather show options for placing the elastic member in the system.

The curved opening 17 for receiving the rod member 80 is formed by inner walls of the clamp 10. In some embodiments, the curved opening 17 has a radius that can accommodate both the rod 80 and the elongate member 80 placed therein. As shown in FIG. 1B, the inner walls of the clamp 10 can include a track or groove 32 formed therein that runs along the inner walls of the clamp 10. The groove 32 advantageously accommodates the elastic member 60 therein. In some embodiments, the groove 32 has a width that is approximately the same as the width of an elastic member 60 positioned therein. With the addition of the groove 32, the clamp 10, rod member 80 and elastic member 60 can be held together, even before tightening the set screw 25 (as discussed below). In some embodiments, the groove 32 runs substantially or completely along the inner walls of the clamp 10.

The curved opening 17 is in communication with a first opening 14 and a second opening 16, each of which extends through the body 12 of the clamp 10. The first opening 14, which runs diagonally relative to a vertical mid-plane of the device, is configured to receive a threaded set screw 25 therein. When the rod member 80 and elastic member 60 have been placed in a desired position within the mouth of the clamp 10, the set screw 25 can be downwardly threaded to apply a compression force on the rod member 80 and elastic member 60 to securely capture the members within the clamp 10.

In some embodiments, a separate bushing 28 can be attached to a distal end of the set screw 25, as shown in FIGS. 1A and 1B. The bushing 28 advantageously provides an intermediary contact surface between the set screw 25 and the elastic member 60, thereby preventing the elastic member 60 from fraying or tearing from the contacting the surface of the set screw 25. As shown in FIG. 1B, the bushing 28 has a curved contact surface 29 that conforms to the shape of the rod member 80 and elastic member 60 positioned in the mouth of the clamp. The curved contact surface 29 advantageously serves as a pressure distribution surface that comfortably distributes pressure around the rod and elastic member 60 as the threaded set screw 25 is downwardly threaded. In other embodiments, the contact surface 29 of the bushing 28 is partially straight. While the set screw 25 and bushing 28 are illustrated as separate components, in other embodiments, the two components are integrated components. The set screw 25 and bushing 28 can be molded together, or can be formed of a monolithic member. In some embodiments, the set screw 25 and the bushing 28 are formed of different materials, while in other embodiments, the set screw 25 and the bushing 28 are formed of the same materials. In some embodiments, the set screw 25 and/or bushing 28 can be formed of different biocompatible metals, such as stainless steel, titanium or cobalt-chrome.

The second opening 16, which runs generally through a vertical mid-plane of the device, is configured to receive one or more elastic members 60 therethrough. As shown in FIG. 1A, this central opening 16 is wide enough to receive two ends or portions of an elastic member 60 that has been looped around a vertebral body. One skilled in the art will appreciate that the positioning of the first and second openings 14 and 16 should not be limited. For example, in alternative embodiments, the positions of the first opening 14 and the second opening 16 can be switched. Alternatively, in other embodiments, the second opening 16 for receiving the ends of the elastic members 60 can be moved away from the vertical mid-plane of the device.

In some embodiments, the elastic member 60 can be a cable. Preferably, the elastic member 60 is a wide elastic band 60. The use of a wide elastic band 60 can advantageously reduce the risk of damage to tissue lacerations or injury. In some embodiments, the elastic band 60 is between 2 and 8 mm, or greater than 4 mm. In some embodiments, the band is composed of a polymer, such as PET. To ensure that the clamp 10 remains secured to a bone member via the elastic band 60, a tensioner can be included as part of the system to make sure that the bands are in proper tension and tightness.

The in-line clamp 10 can be used as follows. In some embodiments, the elastic member 60 (e.g., band) can first be introduced to the clamp 10 without the rod 80 inserted therein. The elastic member 60 can be positioned along and within the single groove 32 that extends along an inner surface of the clamp, which advantageously helps to center the elastic member 60. Both ends of the elastic member 60 can extend through the second hole 16, thereby forming a loop at the bottom of the elastic member 60. The loop of the elastic member 60 can be wrapped around a portion of a spine (not shown), such as a lamina. With the elastic member 60 in place, a rod member 80 can be received through the bottom opening 17 of the clamp 10. Once the rod member 80 is pushed through the bottom opening 17 of the clamp 10 and against the inner walls of the clamp, the rod member 80 is provisionally held in the clamp 10. At this time, the rod member 80 is advantageously free to translate along the direction of its longitudinal axis.

With the rod member 80 in the clamp, a tensioner can be used to tension the elastic member 60, thereby pulling the spine to the rod member 80 in order to correct a deformity. When adequate correction is obtained, the set screw 25 can be downwardly threaded to tighten and securely capture the elastic member 60 and rod member 80. The bushing 28, which serves as either a floating piece that is separate from the set screw 25 or an integrally formed piece with the set screw 25, is positioned at the distal end of the set screw 25 to distribute the tightening load of the set screw 25 uniformly across the elastic member 60 and the rod member 80. As the set screw 25 is downwardly threaded, the set screw 25 compresses against the elastic member 60 and rod member 80, thereby securing the system. At this time, the rod member 80 is locked in place and is no longer free to translate.

Figure 2B:
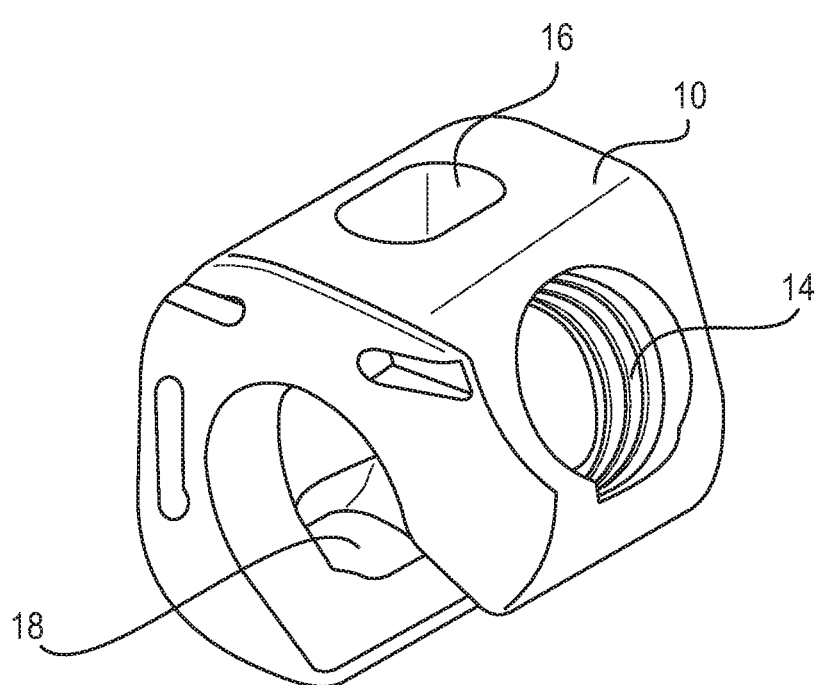
FIG. 2B is a top perspective view of the in-line clamp in FIG. 2A.
Figure 2C:
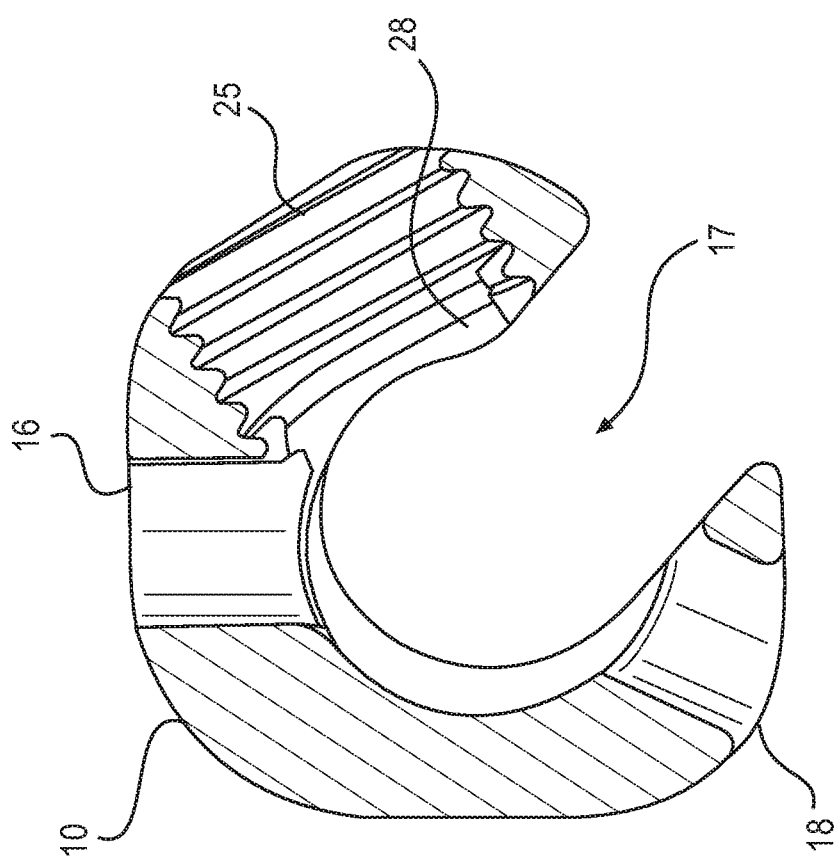
FIG. 2C is a side cross-sectional view of the in-line clamp in FIG. 2A.

FIGS. 2A-2C illustrate different views of an alternate in-line clamp 10 according to some embodiments. The in-line clamp 10 in these figures differs from the clamp in FIGS. 1A and 1B in that it has a first opening 14, a second opening 16 and an additional third opening 18 that extends through the body of the clamp. As shown best in FIG. 2A, the additional third opening 18 is configured to receive two portions or strands of a looped elastic member 60, which also extend into the second opening 16. In addition, while the curved opening 17 opens downward such that the rod member 80 remains bottom-loaded, the curved opening 17 is now more diametrically positioned relative to a vertical mid-plane of the device.

In this embodiment, the elastic member 60 passes through both the second opening 16 and the third opening 18. A loop is formed by the elastic member 60 closer to the third opening 18 and is capable of wrapping around a bone member. In the present embodiments, when a rod member 80 is positioned in the curved opening 17 of the clamp 10, the elastic member 60 is kept on one side of the rod member 80. In other words, the elastic member 60 is positioned between the rod member 80 and the inner walls of the clamp 10, as shown in FIG. 2A. The addition of the third opening 18 thus provides additional ways to accommodate the elastic member 60 relative to the rod member 80 and the clamp 10.

Figure 3A:
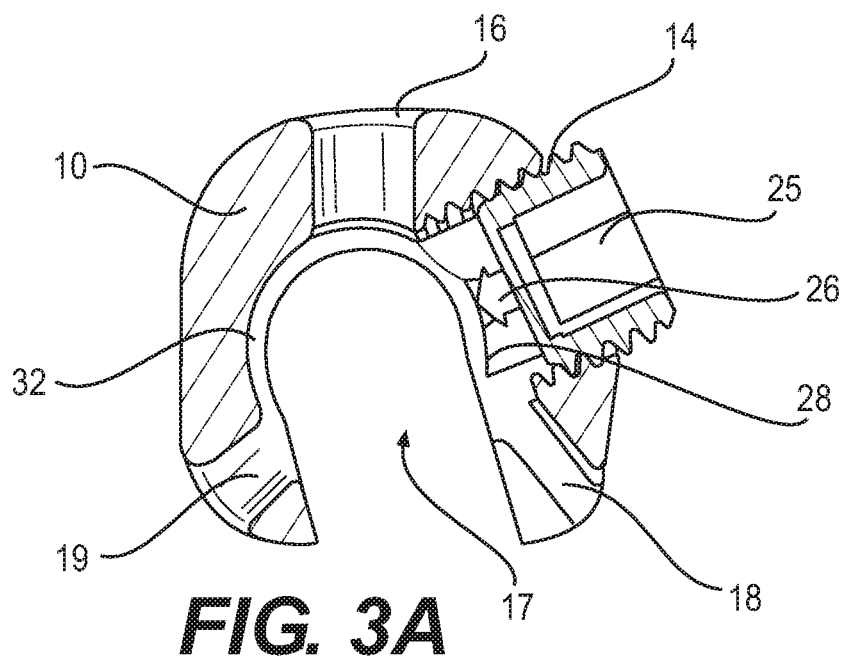
FIG. 3A is a side cross-sectional view of an alternative in-line clamp according to some embodiments.
Figure 3B:
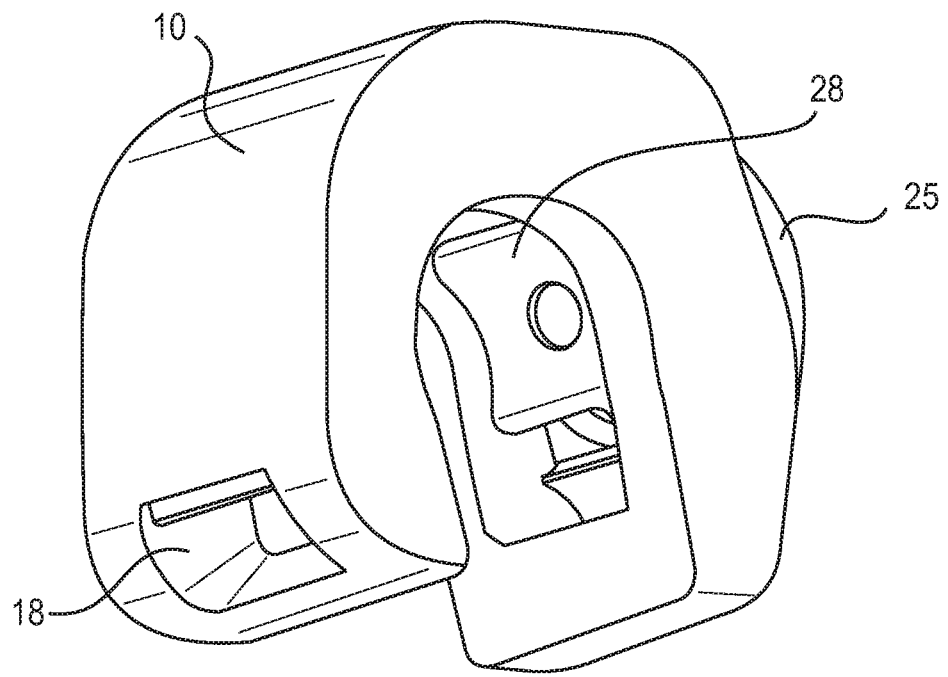
FIG. 3B is a top perspective view of the clamp in FIG. 3A.

FIGS. 3A and 3B illustrate different views of an alternative in-line clamp 10 according to some embodiments. The in-line clamp 10 in these figures differs from the clamp in FIGS. 1A and 1B in that it has a first opening 14, a second opening 16, additional third and fourth openings 18, 19, and a unique set screw 25 having an extension member 26. Both the third opening 18 and the fourth opening 19 are in communication with the opening 17 for receiving a rod member, and are positioned near a lower portion of the clamp 10.

The clamp 10 is configured to receive an elastic member 60 therethrough. In some embodiments, a first end of the elastic member 60 can extend through the third opening 18 while a second end of the elastic member 60 can extend through the fourth opening 19, such that both the first and second ends of the elastic member 60 meet and pass through the second opening 16. A loop is formed at the bottom of the elastic member 60 to receive a bone member. In alternate embodiments, a first end of the elastic member 60 and a second end of the elastic member 60 can pass through the third opening 18 and through the second opening 16 (similar to as shown in FIG. 2A). In yet further alternate embodiments, a first end of the elastic member 60 and a second end of the elastic member 60 can pass through the fourth opening 19 and through the second opening 16. With the latter two options, the elastic member 60 can be kept to generally one side of a rod member 80 inserted into the clamp 10. Accordingly, with the addition of the third opening 14 and the fourth opening 19, this advantageously provides a number of different options for securing the clamp to bone.

The clamp 10 includes a unique set screw 25 having an extension member 26 formed on a distal end thereof. As shown in FIG. 3A, the extension member 26 is a shaped protrusion that can extend through the bushing 28. When the elastic member 60 passes along the inner walls near the bushing 28 (e.g., while entering or exiting the fourth opening 19), the extension member 26 of the set screw 25 is advantageously configured to contact a portion of the elastic member 60 positioned therein. This additional contact provided by the extension member 26 of the set screw 25 helps to advantageously stabilize the elastic member 60 and, along with the bushing 28, helps to distribute the compressive load that occurs during downward threading of the screw 25. In some embodiments, the extension member 26 comprises a blunt tip to reduce the likelihood of fraying of the elastic member 60.

FIGS. 4A-4D illustrate different views of an off-set clamp according to some embodiments. The off-set clamp 100 is configured to receive an elastic member 60 (e.g., through slot or opening 116) on one side of the clamp 100, and a rod member 80 on an opposite side of the clamp 100. The clamp 100 comprises an upper plate 110 having a first opening 114 and a second opening 116 and a lower plate 120. The first opening 114 is configured to receive a set screw 125 that extends through the upper plate 110 and the lower plate 120. The second opening 116 is configured to receive an elastic member 60 as discussed below.

Figure 4A:
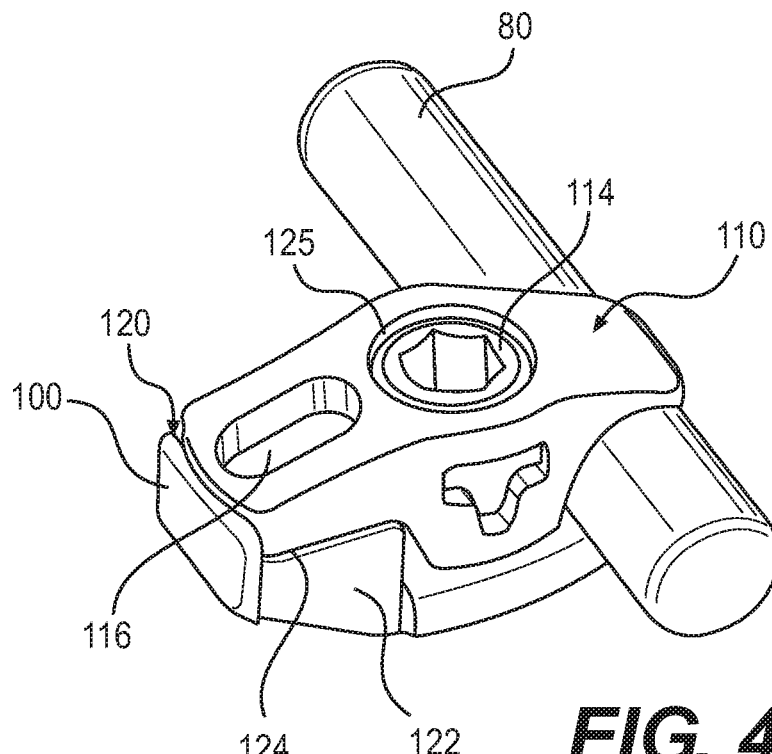
FIG. 4A is a top perspective view of an off-set clamp according to some embodiments.
Figure 4B:
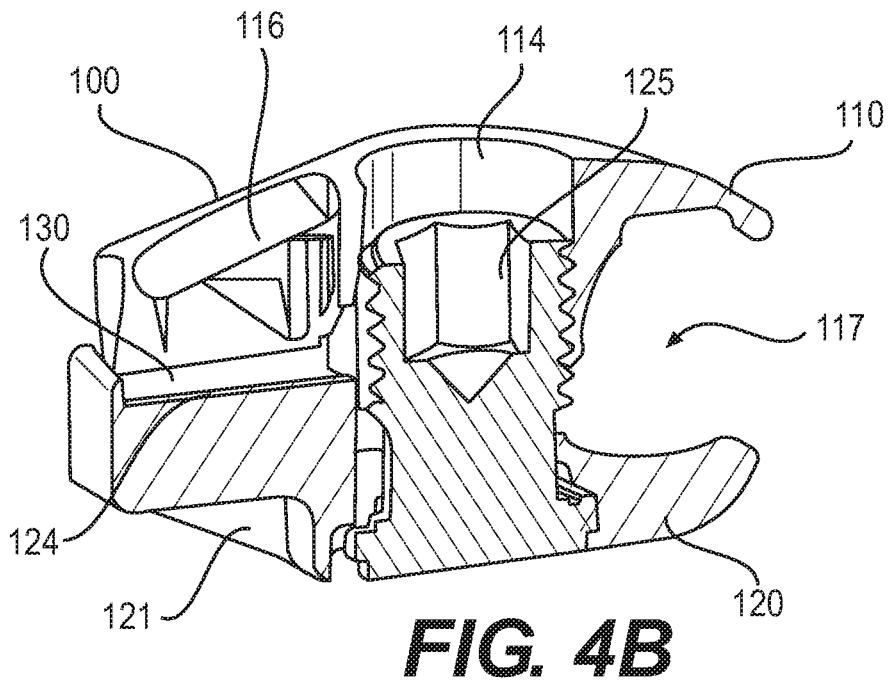
FIG. 4B is a cross-sectional view of the off-set clamp in FIG. 4A.
Figure 4C:
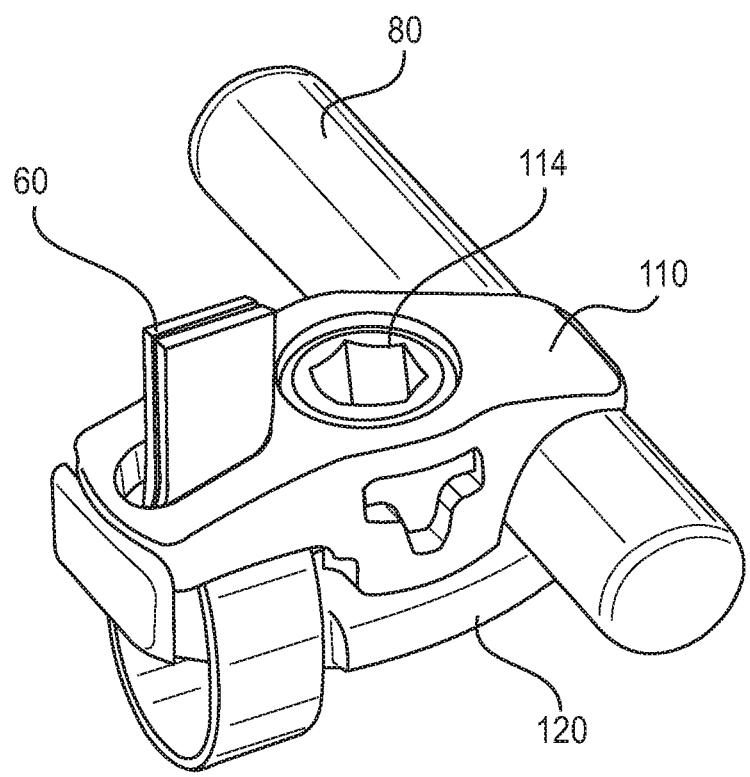
FIG. 4C is a top perspective view of the off-set clamp in FIG. 4A with an elastic member.
Figure 4D:
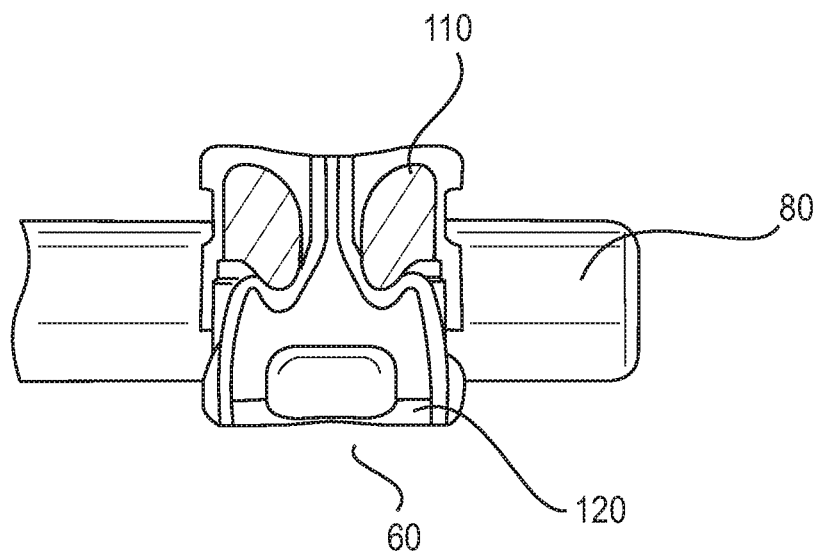
FIG. 4D is a cross-sectional view of the off-set clamp in FIG. 4A with an elastic member.

As shown in FIG. 4B, the upper plate 110 can be physically separated and lifted away from the lower plate 120, thereby providing a space 130 for receiving one or more portions of an elastic member 60 therethrough. In some embodiments, the upper plate 110 can translate both vertically and rotationally relative to the lower plate 120, thereby providing a large enough space 130 (shown in FIG. 4B) for receiving an elastic member 60. The elastic member 60 can form a loop that extends around a bone member, with a first portion of the elastic member 60 in contact with a first lower surface 121 of the lower plate 120 and a second portion of the elastic member 60 in contact with a second lower surface (not shown) on the opposite side of the lower plate 120. The elastic member's trajectory is shown in FIGS. 4C and 4D. In some embodiments, the lower surfaces 121 of the lower plate 120 can comprise an overhang for receiving the elastic member 60 to prevent the elastic member from sliding off of the assembly. With the portions of the elastic member 60 in contact with the lower portions of the lower plate 120, first and second ends of the elastic member 60 can be inserted through the space 130 (shown in FIG. 4B) created when the upper plate 110 is separated from the lower plate 120. The first and second ends of the elastic member 60 can then be inserted through the slot 116 formed in the upper plate 110.

With the elastic member 60 in place such that it is looped around a bone member and such that both of its ends pass through the slot 116, the upper plate 110 can be brought downwardly onto the lower plate 120, thereby securing the elastic member 60 therein. To ensure that the upper plate 110 is secure to the lower plate 120, the set screw 125 can be downwardly threaded, thereby compressively bringing the upper plate 110 into a secure relationship with the lower plate 120. Advantageously, the downward threading of the set screw 125 will also secure a rod member 80 received in the rod opening 117 formed on the opposite ends of the clamp 100. In other words, in some embodiments, the downward threading of the set screw 125 will both secure the elastic member 60 within the upper and lower plates on one side of the clamp 100, and simultaneously secure an off-set rod member 80 that is positioned in a rod opening 117 on an opposite side of the clamp 100.

When the upper plate 110 is removed from the lower plate 120 (e.g., vertically and/or rotationally) such that an elastic member 60 can be received in the space 130, the clamp 100 can be considered to be in an "open" or "unlocked" configuration. When the upper plate 110 is downwardly secured to the lower plate 120 (e.g., via the set screw 125) such that the elastic member 60 is secured within the upper plate 110 and the lower plate 120, the clamp 100 can be considered to be in a "closed" or "locked" configuration.

The off-set clamp 100 can be used as follows. When the clamp is ready to receive the elastic member 60 and rod member 80, the upper plate 110 can be raised and rotated slightly from the lower plate 120 to provide room (e.g., space 130) for inserting an elastic member (e.g., band) 60 between the upper plate 110 and the lower plate 120. The elastic member can wrap around a spinal portion (e.g., a lamina), and can extend along the outer, bottom side walls 121 of the lower plate 120. The bottom side walls 121 of the lower plate 120 can include an overhang to prevent the elastic member 60 from sliding off the clamp 100. Both ends of the elastic member 60 can continue to extend through the slot 116 formed in the upper plate 110. On the opposite side of the clamp 100, a rod member 80 can be received between the upper plate 110 and the lower plate 120. Before tightening the set screw 125 that extends between the upper plate 110 and the lower plate 120, the rod member 80 is provisionally held in the clamp 100 and is advantageously free to translate along its longitudinal axis. With the elastic member 60 wrapped around a bone member and the clamp 100, and the rod member 80 received on the opposite end, the set screw 125 can be tightened such that the clamp 100 clamps down on both the elastic member 60 and rod member 80. This advantageously secures both the elastic member 60 between the upper plate 110 and lower plate 120 on one side of the clamp 100, and the off-set rod member 80 within the rod opening 117 on the opposite side of the clamp 100.

Figure 5A:
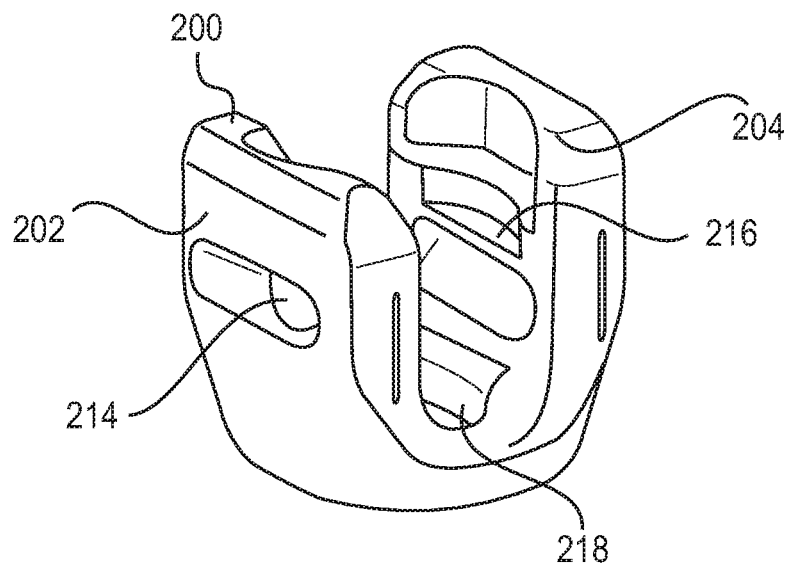
FIG. 5A is a top perspective view of a tulip clamp according to some embodiments.
Figure 5B:
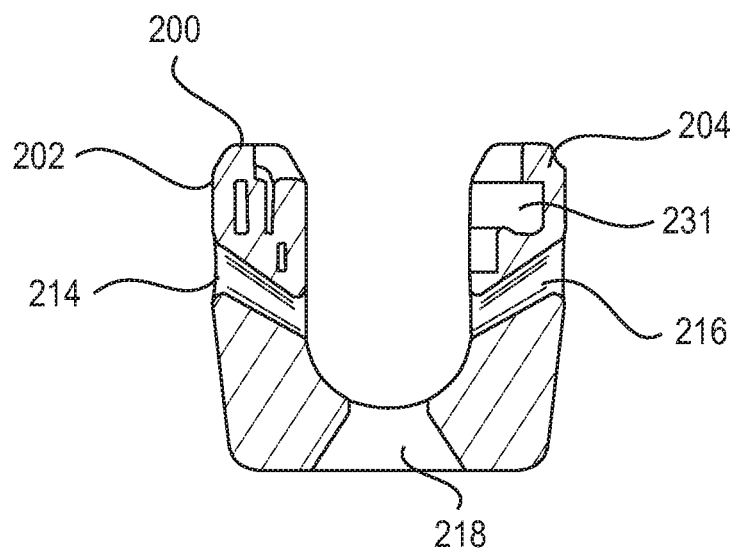
FIG. 5B is a side cross-sectional view of the tulip clamp in FIG. 5A.

FIGS. 5A and 5B illustrate different views of a tulip clamp according to some embodiments. The tulip clamp 200 comprises a first arm 202 and an opposing second arm 204 that join at a base, thereby forming a U-shaped channel for receiving a rod member 80. The first arm 202 comprises a first angled slot or opening 214 for receiving a first end of an elastic member 60 therethrough and the second arm 204 comprises a second angled slot or opening 216 for receiving a second end of the elastic member 60 therethrough. The bottom of the elastic member 60 can form a loop that passes through a third opening 218 formed at the base of the tulip clamp. The loop is capable of looping around a bone member, such as a lamina.

Advantageously, as shown in FIG. 5B, the third opening 218 of the tulip clamp 200 has slanted inner walls. These inner walls advantageously serve as a guide for first and second portions of the elastic member 60 prior to the elastic member 60 opening into a loop below the clamp 200. In some embodiments, the third opening 218 has a width that is greater than a maximum width of the first opening 214 and/or the second opening 216.

The tulip clamp 200 can be used as follows. An elastic member 60 can first be inserted through the tulip clamp 200 by passing first and second ends of the elastic member 60 through the base opening 218. The first end of the elastic member 60 can pass through the angled slot or opening 214, while the second of the elastic member 60 can pass through the angled slot or opening 216. The bottom of the elastic member 60 forms a loop that can be wrapped around a spinal portion, such as a lamina. With the elastic member 60 in place, a rod member 80 can be introduced into the U-shaped channel of the tulip head, such that the elastic member 60 contacts the rod member 80 on two sides. After the rod member 80 is delivered downwardly into the tulip head, a locking cap including a set screw (not shown) can be delivered onto the rod member 80. In some embodiments, the locking cap can rest in locking cap slots 231 found in the arms. In some embodiments, the set screw is threaded and interacts with threads on the arms of the tulip clamp. In other embodiments, in lieu of a set screw and locking cap, a single non-threaded locking cap can be provided. Prior to locking the set screw, the rod member 80 can be provisionally captured such that it is advantageously free to move along its longitudinal axis. With the elastic member 60 and rod member 80 in place, a tensioner can tension the band to pull the spine up to the rod member 80 to correct a deformity. Once the deformity is corrected by tensioning the band, the set screw in the locking cap can be downwardly tightened to secure the rod member 80 and elastic member 60 within the tulip clamp 200.

The clamps discussed above can be accompanied by one or more instruments to facilitate insertion and implantation. For example, in order to properly install a clamp, a tensioner may be used to help tension the elastic member while it is wrapped around a bony structure. The tensioner can hold the elastic member in a corrected position until the set screw of the clamp is finally tightened to securely hold the construct. Accordingly, the clamps can be accompanied by at least two instruments—a holder instrument to facilitate insertion and delivery of the clamp, and a tensioner instrument to hold the elastic band in tension prior to securing the construct.

Figure 6:
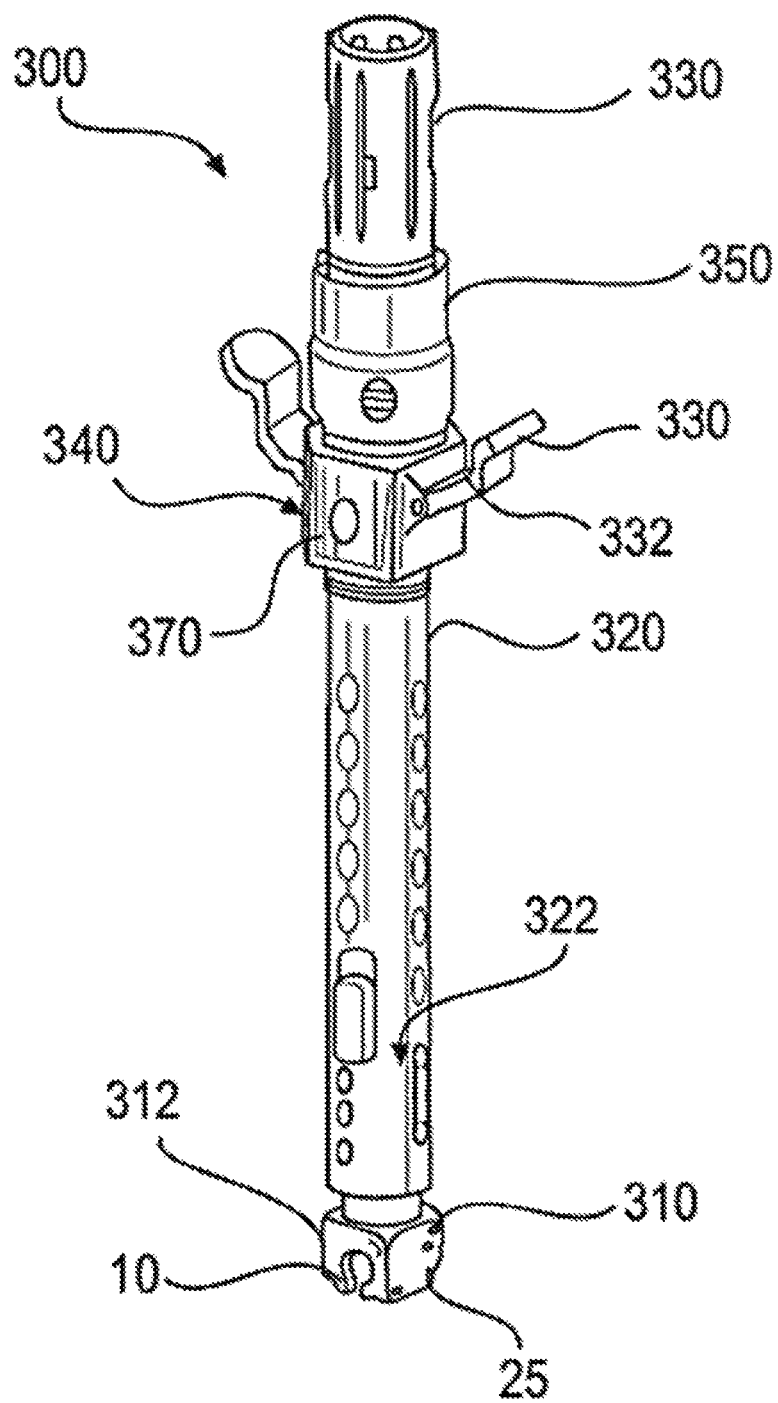
FIG. 6 is a top perspective view of an integrated holder and tensioner instrument according to some embodiments.

Alternatively, a novel integrated holder and tensioner instrument can be provided to facilitate insertion and implantation of a clamping assembly. FIG. 6 is a top perspective view of an integrated holder and tensioner instrument according to some embodiments. By providing an integrated holder and tensioner, the instrument advantageously reduces the need for multiple instruments, and provides a secure means for installing the clamp and elastic member assembly securely.

As shown in FIG. 6, the integrated holder and tensioner instrument 300 comprises a distal portion comprising a clamp holder 310 for holding a clamp. The clamp holder 310 is operatively connected to an outer sleeve 320 which includes one or more slots 322 through which an elastic member can pass therethrough. Adjacent to a proximal portion of the outer sleeve 320 is an elastic member lock base or carriage 340 and an elastic member lock 330, the latter of which is also designed to receive an elastic member therethrough. The integrated instrument 300 further includes a tensioner driver 350 for tensioning an elastic member and a clamp holder handle 300 for opening and closing the clamp holder 310. Each of these components is discussed in greater detail below.

Figure 7:
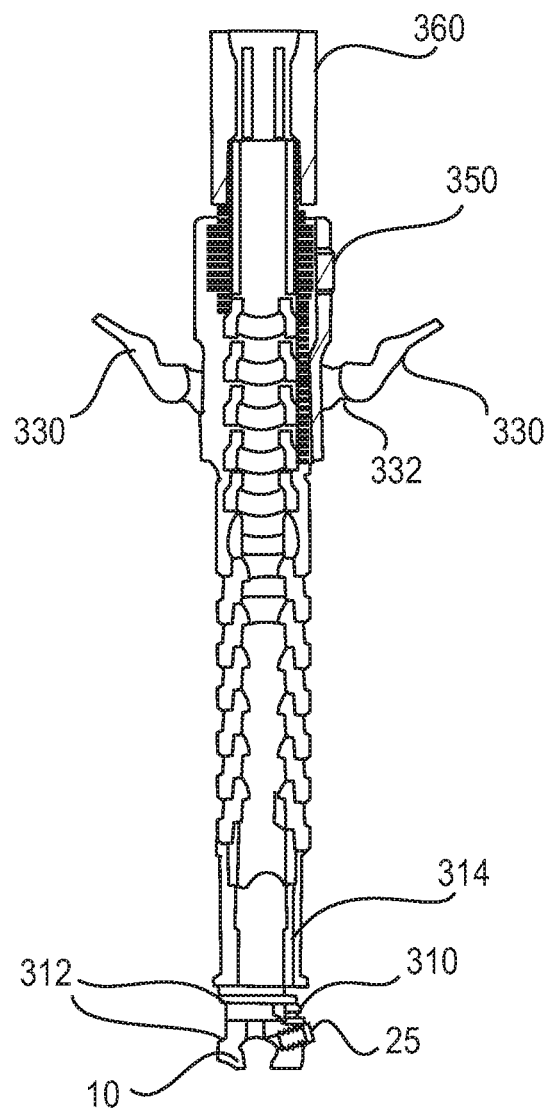
FIG. 7 is a front cross-sectional view of the integrated holder and tensioner instrument of FIG. 6.

In some embodiments, a distal portion of the instrument 300 comprises a clamp holder 310 for receiving a clamp therein. The clamp holder 310 comprises a pair of fingers or tips 312 that can flex open to receive a clamp therein. The tips 312 are capable of flexing via flexible slits or cuts 314, as shown in FIG. 7. The clamp holder 310 can have two configurations: an "open" configuration, whereby it is capable of provisionally and gently holding a clamp therein, and a "closed" configuration, whereby it grips the clamp therein securely and tightly. The clamp holder 310 can be in the open configuration when it first grasps a clamp 10 therein. Once the clamp 10 is provisionally captured in the clamp holder 310, the clamp holder 310 can be placed in a closed configuration to tighten the grip on the clamp 10. This can be accomplished by rotating the clamp holder handle 360, which causes the outer sleeve 320 to translate downwardly onto the clamp holder 310, thereby preventing the tips 312 of the clamp holder 310 from flexing open.

The outer sleeve 320 comprises an elongate body that is operably attached to the clamp holder 310. A distal portion of the outer sleeve 320 is configured to include a pair of elongated slots 322. The elongated slots 322 are configured to receive the ends of the elastic member after the elastic member has been passed through the clamp (as shown in FIG. 1A) and into the distal end of the outer sleeve 320. Each end of the elastic member can pass through a slot 322 formed in the outer sleeve and can extend along the length of the outer sleeve, whereby they can be received in the elastic member locks 330.

The elastic member locks 330 comprise a pair of "wing" shaped members designed to receive an elastic member therein. In some embodiments, each of the elastic member locks 330 comprises an opening or slit 332 for receiving and capturing an end of the elastic member. As the elastic member passes through an elastic member lock 330, the elastic member lock 330 captures and secures the elastic member via a one-way, unidirectional auto-tightening mechanism, thereby preventing the elastic member from backing out from the elastic member lock 330. In other words, an elastic member that passes through the elastic member lock 330 can be pulled in tension, without worrying about backing out of the elastic member. The one-way, auto-tightening mechanism can comprise different types of mechanisms, including cam, grooved, flat, and/or rounded surfaces whereby once engaged, they prevent sliding of the elastic member within the lock 330. When desired, an elastic member can be released from an elastic member lock 330 by pressing the elastic member lock 330 downwardly, thereby actuating a release function.

The elastic member locks 330 are positioned adjacent to the elastic member lock base or carriage 340 and the tensioner driver 350, which work in conjunction to place the ends of the elastic member in tension. By rotating the tensioner driver 350, this causes the elastic member lock base or carriage 340 to translate along the longitudinal axis of the outer sleeve in a proximal direction away from the clamp 10. This movement of the elastic member lock base 340 pulls on the elastic member, thereby placing the ends of the elastic member (which are constrained to the elastic member locks 330) in greater tension.

In addition to these features, the integrated instrument 300 includes a clamp holder handle 360 positioned at a proximal portion of the instrument 300. As discussed earlier, the clamp holder handle 360 is capable of actuating the outer sleeve 320, thereby causing the clamp holder 310 to be in an "open" or "closed" position.

Methods for using the integrated holder and tensioning instrument 300 are now described. In some embodiments, a surgeon would select a clamp 10 to be inserted into a patient. The surgeon can then engage the instrument 300 to the clamp 10 via the clamp holder 310. The clamp holder 310 is in an "open" configuration, and is only provisionally engaged with the clamp 300. After provisionally engaging the clamp holder 310 to the clamp 10, an elastic member (e.g., a band) can be passed through the clamp 10 and out through the clamp holder 310 and the slots 322 of the outer sleeve 320. In addition to retaining the clamp 10, the clamp holder 310 can be used to provisionally retain a rod member that is forced into the clamp 10. With the rod and elastic member provisionally retained within the clamp 10 and clamp holder 310, the surgeon can rotate the clamp holder handle 360 to place the clamp holder 310 in a "locked" configuration, thereby tightening the grip on the clamp 10.

At this time, the ends of the elastic member can be passed through the elastic member locks 330, thereby securely capturing the ends. Once the ends of the elastic member are captured in the elastic member locks 330, the tensioner driver 350 can be rotated to place further tension on the elastic member's ends. Once the elastic member has been placed in a desired amount of tension, the surgeon can use a hex driver to tighten the set screw 25 of the clamp 10 to thereby secure the clamp member, rod member and elastic member. As the clamp 10 and its associated elastic member are now assembled, the surgeon can either (i) unlock the elastic member locks 330 to slide the elastic member ends out or (ii) cut the elastic member on either side without unlocking the elastic member locks. The clamp holder 360 can then be rotated to disengage the instrument 300 from the installed clamp 10, thereby allowing the instrument 300 to be removed from the assembled clamp construct in the patient. Optionally, as the ends of the elastic member are loose, the surgeon may choose to cauterize the ends to prevent fraying of the loose ends.

In addition to the components discussed above, the integrated holder and tensioner instrument 300 can further include other components. In some embodiments, the tensioner instrument 300 can be accompanied by a counter torque device (not shown) that can be attached to the counter torque attachment surface 370 on the elastic member base 340. The counter torque device helps to limit rotation to only those component necessary when rotating the tensioner driver. In addition, the tensioner instrument 300 can also be accompanied by a secondary handle that attaches to the clamp handle 360 to limit or indicate the amount of torque being applied, thereby advantageously preventing over-tensioning of the elastic member.

FIG. 7 is a front cross-sectional view of the integrated holder and tensioner instrument of FIG. 6. From this view, one can see the cross-section of the clamp holder 310, including the flexible cuts or slits 314 that enable flexion of the clamp holder tips 312.

Figure 8:
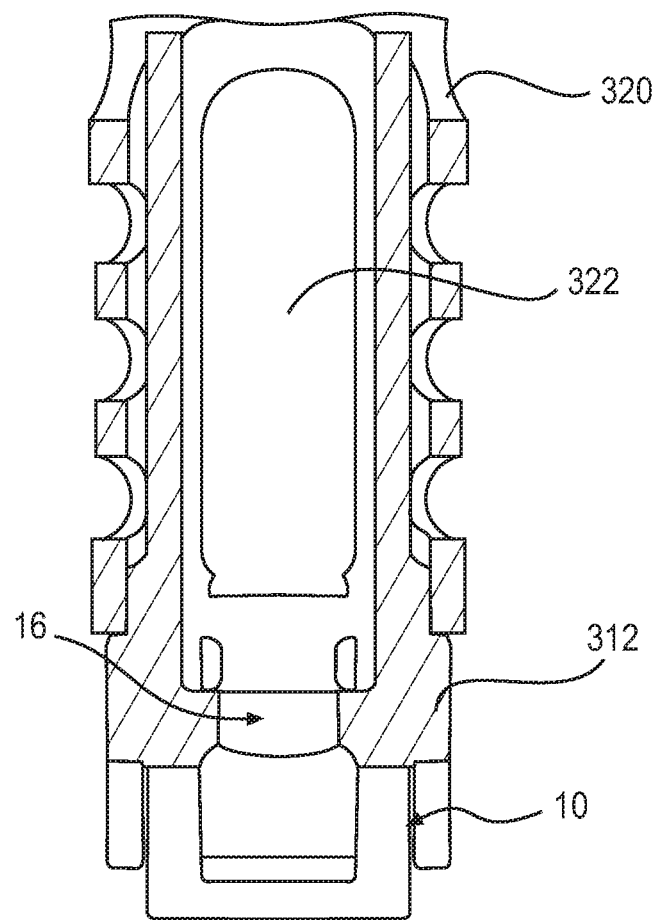
FIG. 8 is a close-up view of a distal portion of the integrated holder and tensioner instrument of FIG. 6.

FIG. 8 is a close-up view of a distal portion of the integrated holder and tensioner instrument of FIG. 6. From this view, one can see the upper opening 16 in the clamp 10 through which the ends of the elastic member can pass before passing through the slots 322 in the outer sleeve 320.

Figure 9:
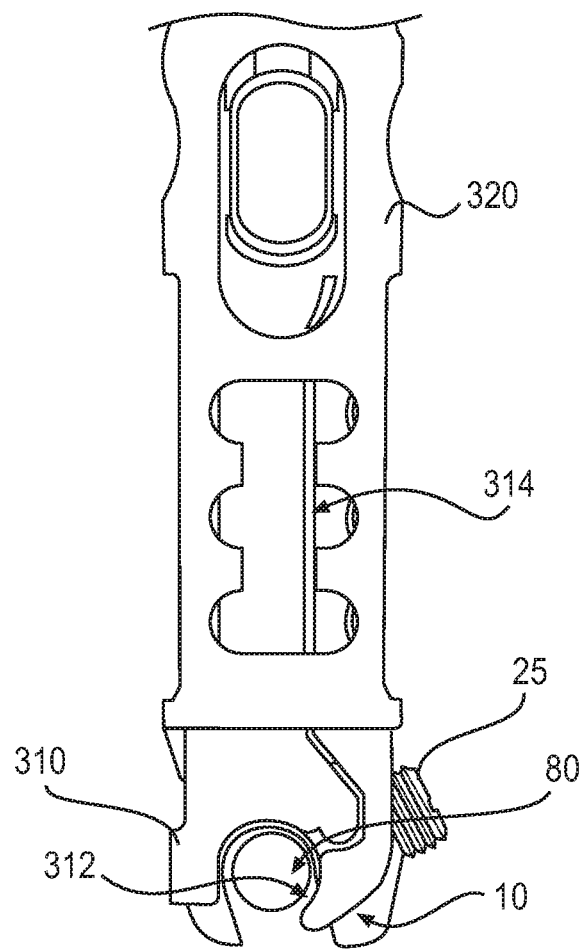
FIG. 9 is an alternate close-up view of a distal portion of the integrated holder and tensioner instrument of FIG. 6.

FIG. 9 is an alternate close-up view of a distal portion of the integrated holder and tensioner instrument of FIG. 6. From this view, one can see a rod member 80 that is provisionally captured in the clamp 10 via the clamp holder 310. To tighten the grip on the rod member 80 and clamp 10, the outer sleeve 320 can be translated downwardly to compress the flexible tips of the clamp holder 310, thereby causing the clamp holder 310 to be in a "closed" tight position.

Figure 10:
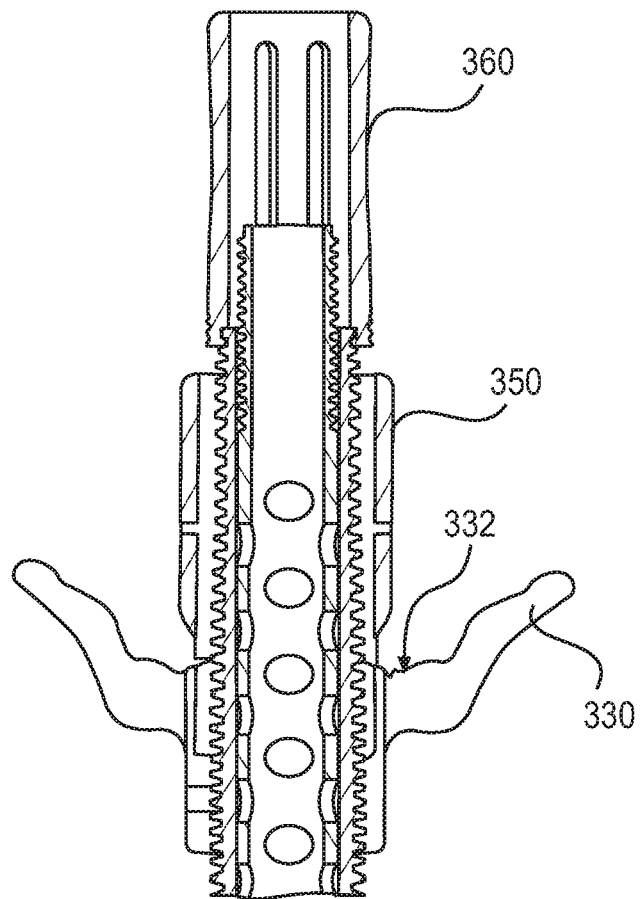
FIG. 10 is a close-up view of a proximal portion of the integrated holder and tensioner instrument of FIG. 6.

FIG. 10 is a close-up view of a proximal portion of the integrated holder and tensioner instrument of FIG. 6. From this view, one can see the opening or slit 332 formed in each of the elastic member locks 330, through which an elastic member can pass through. The slit 332 serves as a contact or locking surface of the elastic member, which is configured to pass through each of the elastic member locks 330 prior to tensioning the elastic member.

Figure 11:
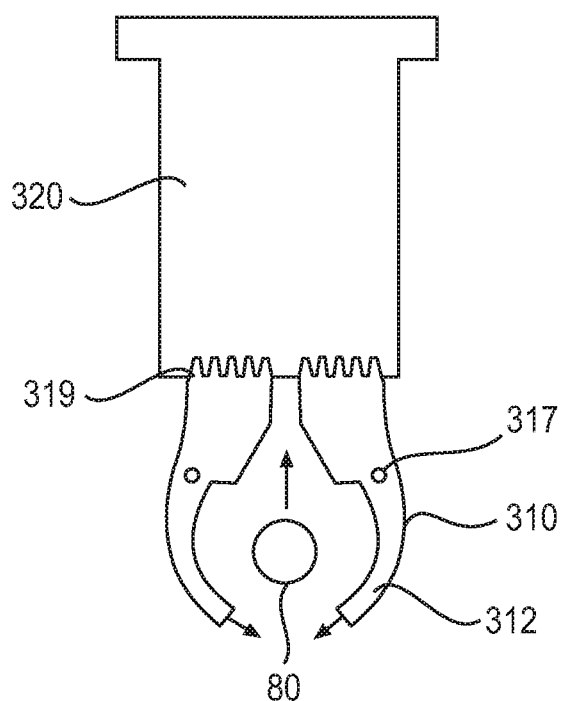
FIG. 11 is a close-up view of a distal portion of an alternate integrated holder and tensioner instrument according to some embodiments.

An alternate design of an integrated holder and tensioner instrument is now described. FIG. 11 is a close-up view of a distal portion of an alternate integrated holder and tensioner instrument according to some embodiments. The instrument in FIG. 11 shares many features with the instrument in FIG. 6, including a clamp holder, an outer sleeve, elastic member locks, an elastic member base, a tensioner driver, and a clamp holder handle. However, in contrast to the instrument in FIG. 6, the instrument in FIG. 11 comprises a clamp holder 310 having a pair of hinged tips 312. The hinges 317 allow the tips 312 to open and close on a clamp and/or rod member similarly to the instrument in FIG. 6. In further contrast to the instrument in FIG. 6, the instrument in FIG. 11 can also include one or more teeth for securing the clamp holder 310 to the outer sleeve 320.

Additional integrated holder and tensioner instruments are shown in FIGS. 12-22. The instruments 400, 500 shown in these embodiments include a number of distinct advantages. In particular, the instruments 400, 500 allow for elastic members to be advantageously side-loaded into the instruments, which allows for ease of engagement between the elastic members and their respective instruments. In addition, the instruments 400, 500 advantageously have lower members 402, 502 that are capable of separation from respective upper members 404, 504. This allows for greater visibility during the surgical procedure, as will be discussed in greater detail below.

Figure 12:
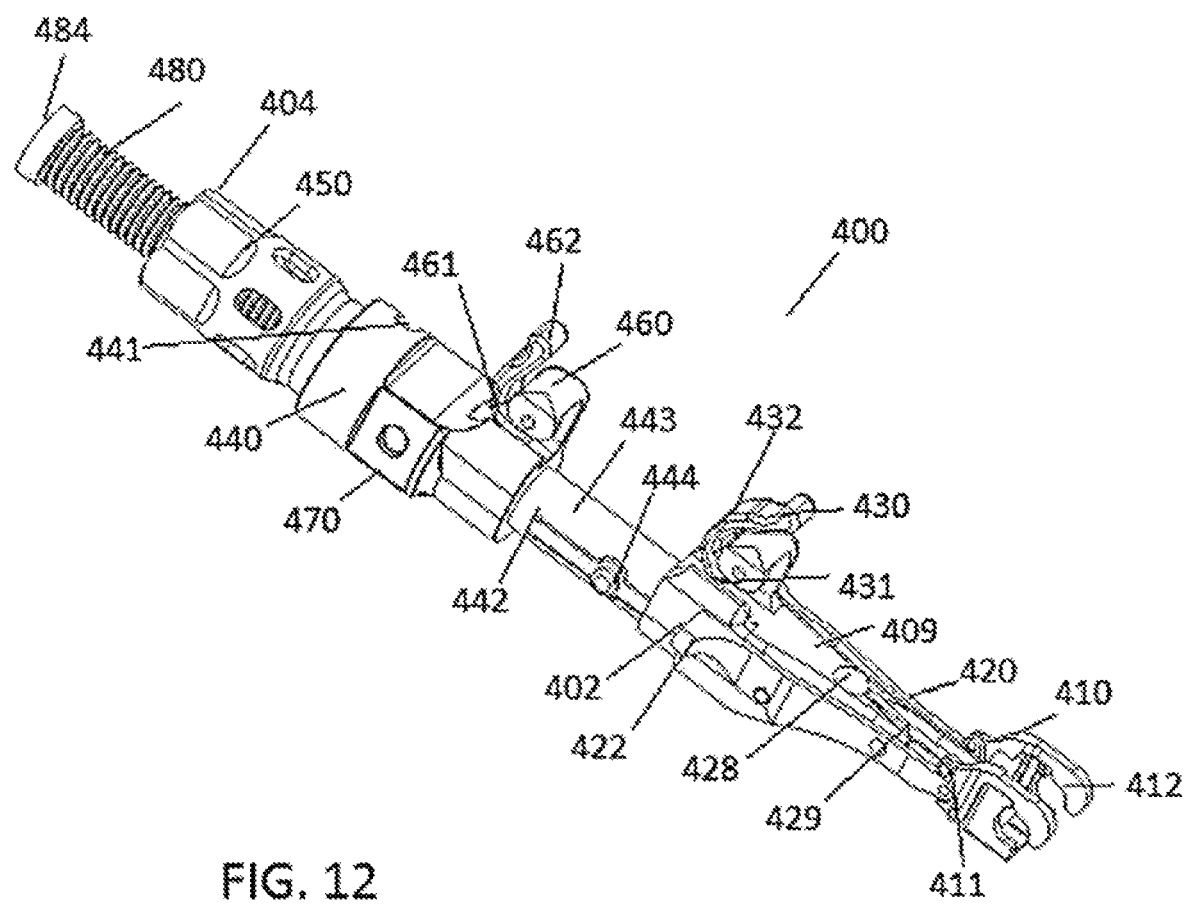
FIG. 12 is a perspective view of an alternative integrated holder and tensioner instrument.

FIG. 12 is a perspective view of an alternative integrated holder and tensioner instrument in accordance with some embodiments. The instrument 400 comprises a lower member 402 and a separable upper member 404. The lower member 402 comprises a bottom cam lock 430 having a side opening 431 for receiving an elastic member therethrough. An upper member 404 is attachable to the lower member 402. The upper member 404 further includes a top cam lock 460 having a side opening 461 for receiving the elastic member therethrough. The top cam lock 460 can be attached to a moveable elastic member lock base or carriage 440. Translation of the carriage 440 (e.g., via a tensioner driver 450) in an upward direction causes the tension on the elastic member to increase, while translation of the carriage 440 in a lower direction reduces tension on the elastic member.

Advantageously, the instrument 400 can allow for sequential reduction of the spine by providing a low profile lower member 402 that can retain tension on the elastic member. The instrument 400 is advantageously designed such that the lower member 402 can be attached to a bone member without the upper member 404 attached thereto. The lower member 402 can then receive a portion of the elastic member therethrough with minimal obstruction. The lower member 402 is designed to advantageously retain tension on the elastic member, while maintaining a low profile prior to attachment of the upper member 404. When the elastic member is ready to be tensioned further, the upper member 404 can simply be fitted onto the lower member 402 (e.g., via a snapfit or connection), and the elastic member can then be received through the top cam lock 460. The tensioner driver 450 can then be rotated, thereby causing upward translation of the carriage 440 and top cam lock 460. This increases the tension in the elastic member.

Figure 14:
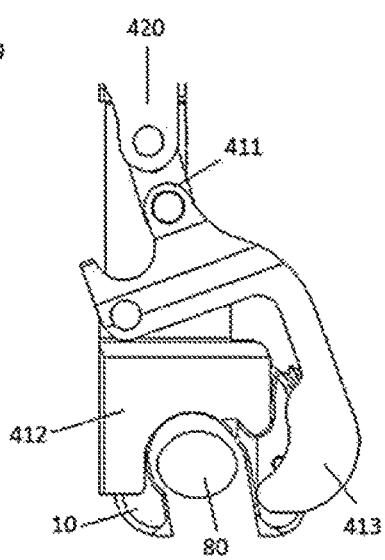
FIG. 14 is a side view of a lower member of the integrated holder and tensioner instrument of FIG. 12.
Figure 15:
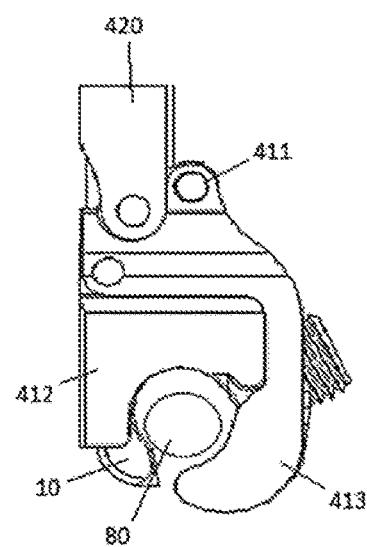
FIG. 15 is a side view of a lower member of the integrated holder and tensioner instrument of FIG. 12.

As shown in FIG. 12, the lower member 402 comprises a shaft 409 having a distal end that is operably attached to a clamp holder 410. A sleeve 420 extends around the shaft 409. The clamp holder 410 comprises at least two sets of fingers or tips 412 that are configured to grip a clamp 10 therein. The clamp holder 410 can comprise proximal nubs or hinges 411 that interact with the sleeve 420, as will be discussed further below. The clamp holder 410 is configured to hold both a clamp 10 and a rod member 80 within the clamp (as shown in FIGS. 14 and 15).

The clamp holder 410 is capable of provisionally retaining a clamp 10 therein simply by applying a downward force on the clamp 10. The shaft 409 of the lower member 402 comprises a cut portion that extends along a longitudinal axis of the lower member 402. In particular, the shaft 409 comprises a circular or rounded flex cut 428 and an elongated cut 429. These cuts 428, 429 advantageously allow the fingers 412 of the clamp holder 410 to spread open, thereby retaining the clamp 10 therein upon application of downward force to the clamp 10.

The clamp holder 410 is also capable of receiving and retaining a rod member 80 within the clamp 10. To retain the rod member 80, the fingers 412 are first moved into a spread "open" configuration, as shown in FIG. 14. To move the fingers into the open configuration, the sleeve 420 can be pulled upward via a pair of wings 422. In some embodiments, the sleeve 420 is spring-loaded. As the sleeve 420 is pulled upward, the distal end of the sleeve 420 is removed from engagement with the proximal nubs 411 of the clamp holder 410, which thereby allows the fingers 412 to spread into the open configuration. With the fingers 412 in the open configuration, a rod member 80 can be delivered into the clamp holder 410. Once the rod member 80 is delivered therein, the wings 422 can be released. Releasing the wings 422 causes the spring-loaded sleeve 420 to return to its original configuration, whereby its distal end is in engagement with the proximal nubs 411 of the clamp holder 410 (as shown in FIG. 12). This moves the fingers 412 into a "closed" configuration, as shown in FIG. 15, which thereby encloses the rod member 80 therein.

The clamp 10 that is retained within the clamp holder 410 can include an elastic member. The elastic member can extend through a side-loaded opening 431 of the bottom cam lock 430, thereby advantageously placing the elastic member in tension. In some embodiments, the bottom cam lock 430 is spring loaded. As the elastic member is extended through the bottom cam lock 430, the spring loaded feature allows the elastic member to be retained within the bottom cam lock 430. To release the elastic member from the bottom cam lock 430, the bottom cam lock 430 comprises a release latch 432. Movement of the release latch 432 enables controlled movement of the elastic member within the bottom cam lock 430 as desired.

The lower member 402 is advantageously capable of attachment to bone member without the upper member 404 attached thereto. This allows for enhanced visibility of the surgical site by providing an instrument that is less obstructive.

As shown in FIG. 12, the upper member 404 comprises a distal shaft 442, an outer shaft 443 that extends around the distal shaft 442, an elastic member lock base or carriage 440 attached to the distal shaft 442, a tensioner driver 450 for translating the carriage 440, and a threaded shaft 480 extending through the tensioner driver 450.

The distal shaft 442 of the upper member 404 comprises a cylindrical shaft that is sized and configured to be received in an opening of the lower member 402. In some embodiments, the distal shaft 442 comprises a smooth outer surface. The distal end of the distal shaft 442 comprises one or more members that allow for a quick connection with the lower member 402 (e.g., via a snap fit).

The outer shaft 443 of the upper member 404 comprises a cylindrical shaft that is sized and configured to extend around the distal shaft 442. In some embodiments, the outer shaft 443 comprises a shaft release button 444. When the release button 444 is pressed down, this disengages the distal shaft 442 from the lower member 402, thereby allowing for removal of the upper member 404 from the lower member 402.

The carriage 440 of the upper member 404 is attached to a proximal end of the outer shaft 443. A top cam lock 460 extends from the carriage 440. The top cam lock 460 comprises a side-loaded opening 461 that allows an elastic member to be side-loaded therein. In some embodiments, an elastic member can be extended through the bottom cam lock 430 and into the top cam lock 460, whereby it can be further tensioned. The top cam lock 460 further comprises a release latch 462. Movement of the release latch 462 releases the elastic member if desired, thereby reducing tension on the elastic member. In some embodiments, the top cam lock 460 is spring loaded, such that upon release of the top cam lock 460, the top cam lock 460 will go back to its original position and retain the elastic member therein. In addition, the carriage 440 of the upper member 404 comprises a counter torque attachment surface 470 which can be gripped by a counter torque device. The counter torque device helps to limit rotation to only those components necessary when rotating the tensioner driver. In some embodiments, the carriage 440 is capable of translation via the tensioner driver 450, thereby increasing the tension on the elastic member.

The tensioner driver 450 of the upper member 404 comprises a cylindrical member that is attached to a proximal end of the carriage 440. The tensioner driver 450 can comprise a base portion that is received in a cut out portion 441 of the carriage 440, thereby retaining the tensioner driver 450 to the carriage 440. The tensioner driver 450 includes internal threads that are configured to engage external threads of the threaded shaft 480. Rotation of the tensioner driver 450 in a first direction causes the tensioner driver 450 to rotate upwardly along the threaded shaft 480. As the tensioner driver 450 is attached to the carriage 440, the carriage 440 also translates upwardly, thereby increasing tension on the elastic member attached to the carriage 440. Rotation of the tensioner driver 450 in a second direction causes the tensioner driver 450 to rotate downwardly along the threaded shaft 480. This causes the carriage 440 to translate downwardly, thereby reducing tension on the elastic member attached to the carriage 440. In some embodiments, the tensioner driver 450 comprises a hex knob.

The threaded shaft 480 of the upper member 404 comprises external threads that engage internal threads of the tensioner driver 450. In some embodiments, the threaded shaft 480 comprises a proximal cap 484. Advantageously, the proximal cap 484 serves as a stop that prevents the tensioner driver 450 from going past the cap, thereby reducing the risk of the tensioner driver 450 from falling off the threaded shaft 480.

The method of using the instrument 400 is as follows. In some embodiments, the lower member 402 is delivered to receive a clamp 10, which can further receive a rod member 80 therein. An elastic member or band that extends through the clamp 10 can be pulled through a side opening or slot 431 of the bottom cam lock 430, thereby placing the elastic member in tension. The upper member 404 can then be delivered into attachment with the lower member 402, whereby it can be attached via a quick connection (e.g., a snap fit). The elastic member can then be pulled through a side opening or slot 461 of the top cam lock 460, whereby it can be retained in further tension. To increase tension on the elastic member, the tensioner driver 450 can be rotated, thereby causing upward translation of the carriage 440 upon which the top cam lock 460 resides. As the carriage 440 is drawn upwardly, this increases the tension on the elastic member. When the elastic member has achieved its desired tension, a set screw 25 (shown in FIG. 1A) can be downwardly threaded onto the elastic member, thereby securing the clamp 10 to bone. The instrument 400 can then be removed from the clamp. First, the upper member 404 can be released from the lower member 402 by pressing the release button 444. Second, the lower member 402 can be released from the clamp 10 by pulling upwardly on the wings 422 of the sleeve 420. This causes the fingers 412 to open, which thereby allows the clamp 10 to disengage from the instrument 400 if desired. In some embodiments, loose ends of the elastic member can be cut while attached to the instrument 400. In other embodiments, loose ends of the elastic member are cut after detachment of the instrument 400 from the elastic member. Any remaining loose ends of the elastic member can be glued, singed, or further cut if desired. At this time, the clamp 10 is securely retained on a bone member.

Figure 13:
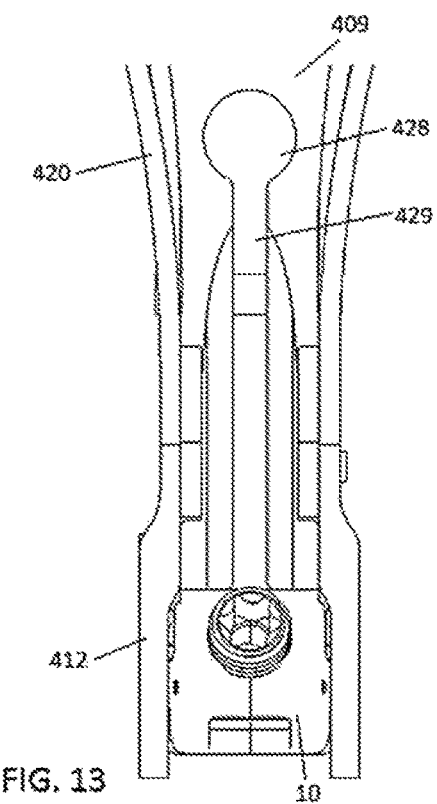
FIG. 13 is a close-up view of a lower member of the integrated holder and tensioner instrument of FIG. 12.

FIG. 13 is a close-up view of a lower member of the integrated holder and tensioner instrument of FIG. 12. From this view, one can see the shaft 409, as well as the rounded flex cut 428 and elongated flex cut 429 formed therein. The flex cuts 428, 429 advantageously help the instrument to retain a clamp 10, simply by downward force onto the clamp 10.

FIG. 14 is a side view of a lower member of the integrated holder and tensioner instrument of FIG. 12. From this view, one can see the fingers 412 in a "open" configuration, whereby a rod member 80 can be received therein. The fingers 412 include at least one hinged portion 413, whereby in the open configuration, the hinged portion 413 is away from the opposing finger, thereby providing room to receive the rod member 80. To maintain the fingers 412 in the open configuration, the sleeve 420 is pulled upwardly via its wings 422.

FIG. 15 is a side view of a lower member of the integrated holder and tensioner instrument of FIG. 12. From this view, one can see the fingers 412 in a "closed" configuration whereby a rod member 80 is secured therein. In the closed configuration, the hinged portion 413 is nearer to the opposing finger, thereby trapping the rod member 80 within the clamp 10. To place the fingers 412 in the closed configuration, a surgeon simply needs to release the wings 422. The spring-loaded action of the sleeve 420 will cause the sleeve to go back to its original location, such that the fingers 412 are placed in the closed configuration.

Figure 16:
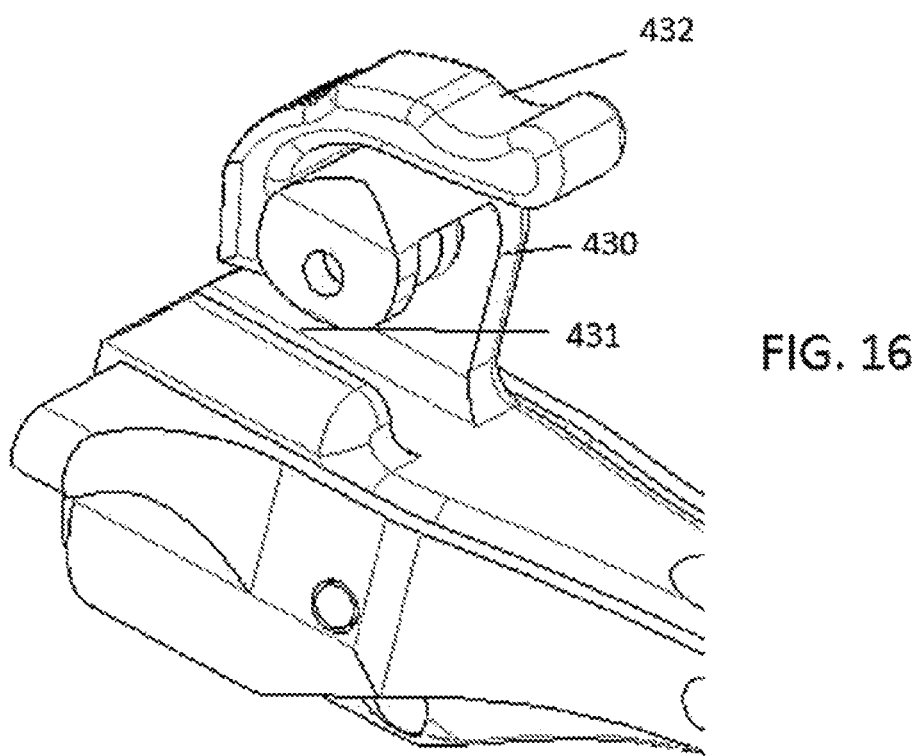
FIG. 16 is a side perspective view of a lower member of the integrated holder and tensioner instrument of FIG. 12.

FIG. 16 is a side perspective view of a lower member of the integrated holder and tensioner instrument of FIG. 12. From this view, one can see the bottom cam lock 430 close up. The bottom cam lock 430 includes a side-loaded opening or slot 431 for easily delivering an elastic member therein.

Figure 17:
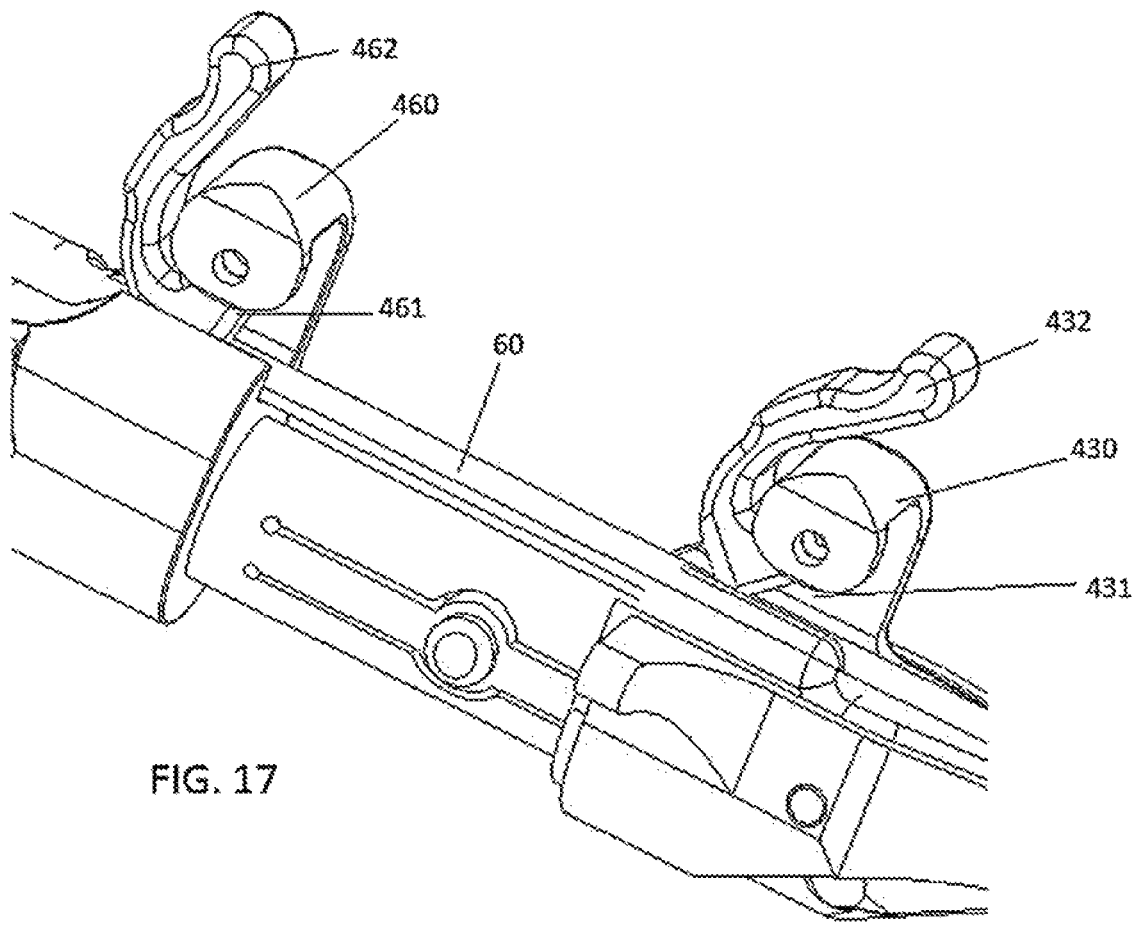
FIG. 17 is a perspective view of cam locks of the integrated holder and tensioner instrument of FIG. 12.

FIG. 17 is a perspective view of cam locks of the integrated holder and tensioner instrument of FIG. 12. From this view, one can see the bottom cam lock 430, the top cam lock 460 and the elastic member 60 that extends between the two cam locks. Advantageously, the elastic member 60 is side-loaded into each of the bottom cam lock 430 and the top cam lock 460, thereby making it easier to retain the elastic member 60 therein.

Figure 18:
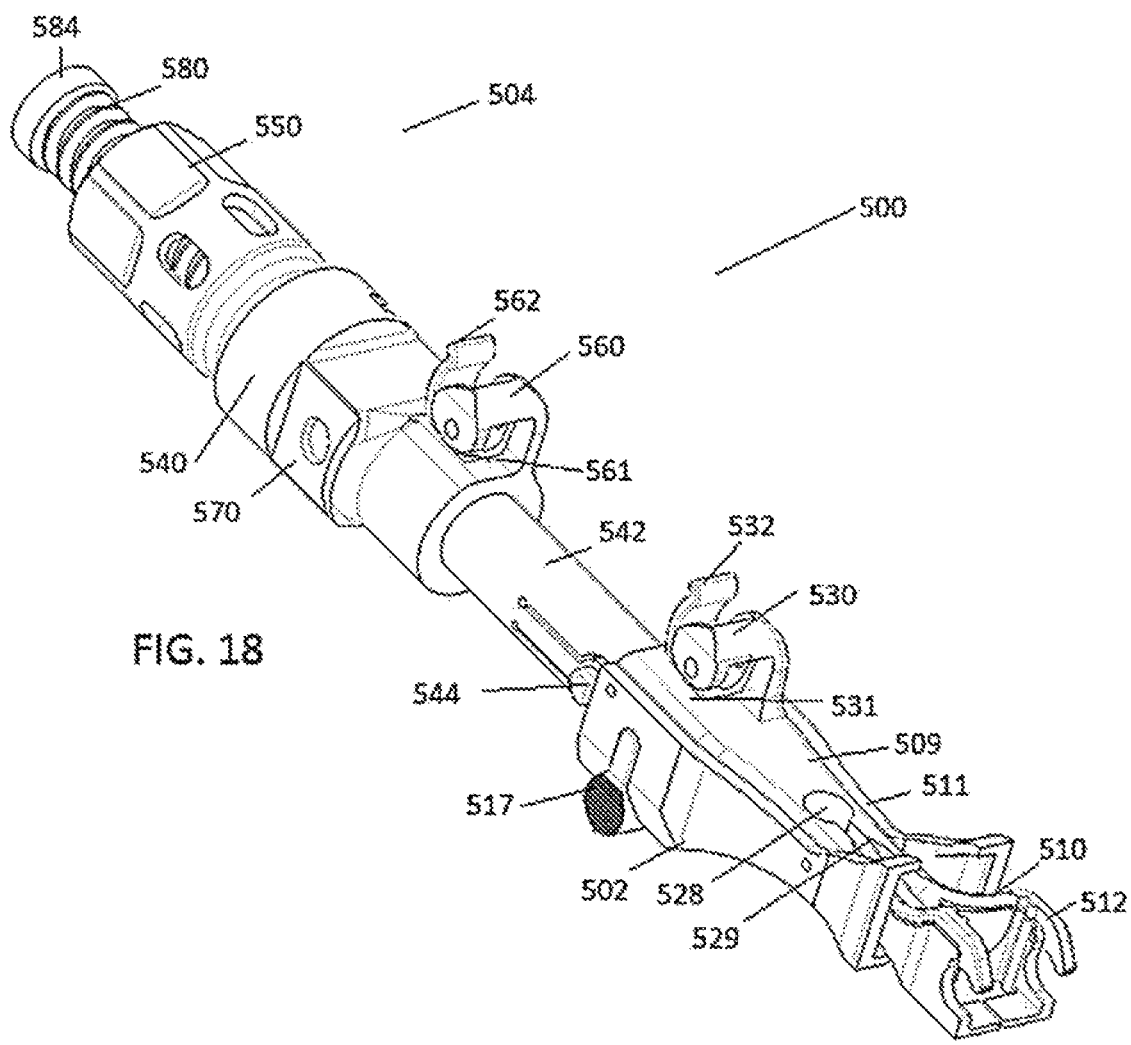
FIG. 18 is a perspective view of an alternative integrated holder and tensioner instrument.

FIG. 18 is a perspective view of an alternative integrated holder and tensioner instrument. The instrument 500 comprises a number of similar features as the embodiment in FIG. 12, including a lower member 502 having distal fingers or tips 512 and an upper member 504 separable from the lower member 502. The lower member 502 comprises a bottom cam lock 530, while the upper member 504 comprises a top cam lock 560, each of which is configured to have an opening or slot 531, 561 for advantageously side loading an elastic member. In some embodiments, the openings 531, 561 are inline and preserve the visibility of the surgical site during use. As shown in FIG. 18, the instrument 500 includes an alternate sleeve 511 for placing the fingers 512 in an open or closed configuration, as will be discussed in more detail below.

The instrument 500 comprises a lower member 502 including a shaft 509 having a rounded flex cut 528 and an elongated flex cut 529. A clamp holder 510 is positioned at a distal end of the shaft 509. The clamp holder 510 comprises sets of fingers or tips 512 designed to retain a clamp 10 and/or a rod member 80 therein. A spring-loaded sleeve 511 extends over the shaft 509 and is designed to place the fingers 512 in a "closed" or "open" configuration. In its natural state, the sleeve 511 extends distally around fingers 512, thereby placing the fingers 512 in a closed configuration. To put the fingers 512 in an open configuration whereby they can receive a clamp 10 and/or rod member 80 therein, a sleeve release button 517 can pushed, thereby freeing the sleeve 511 such that it can moved along a longitudinal path. In some embodiments, the sleeve 511 is capable of being moved along a longitudinal path simply by pushing the sleeve release button 517. With the sleeve release button 517 pushed, the sleeve 511 can be moved upwardly or downwardly, thereby placing the fingers 512 in a "closed" or "open" configuration as desired.

In addition, the lower member 502 further comprises a bottom cam lock 530 having an opening or slot 531 that allows for side-loading of an elastic member. In some embodiments, the bottom cam lock 530 is spring-loaded. To release the elastic member, a release latch mechanism 532 is provided. The release latch mechanism 532 allows for the release of an elastic member once it has been received through the side opening 531.

The instrument 500 further comprises an upper member 504 including a distal shaft 542, a lock base or carriage 540 attached to the proximal end of the distal shaft 542, a tensioner driver 550 attached to the carriage 540 and a threaded shaft 580 extending through the carriage 540. Advantageously, in some embodiments, the upper member 504 is separable from the lower member 502. This way, the lower member 502 can be inserted near a surgical site without the upper member 504, and an elastic member can be received and tensioned via the lower member 502 without obstruction from the upper member 504.

The distal shaft 542 of the upper member 504 comprises a cylindrical shaft that is sized and configured to be received in an opening of the lower member 502. In some embodiments, the distal shaft 542 comprises a smooth outer surface. The distal end of the distal shaft 542 comprises one or more members that allow for a quick connection with the lower member 502 (e.g., via a snap fit).

The carriage 540 of the upper member 504 is attached to a proximal end of the distal shaft 542. A top cam lock 560 extends from the carriage 540. The top cam lock 560 comprises a side-loaded opening 561 that allows an elastic member to be side-loaded therein. In some embodiments, an elastic member can be extended through the bottom cam lock 530 and into the top cam lock 560, whereby it can be further tensioned. The top cam lock 560 further comprises a release latch 562. Movement of the release latch 562 releases the elastic member if desired, thereby reducing tension on the elastic member. In some embodiments, the top cam lock 560 is spring loaded, such that upon release of the top cam lock 560, the top cam lock 560 will go back to its original position and retain the elastic member therein. In addition, the carriage 540 of the upper member 504 comprises a counter torque attachment surface 570 which can be gripped by a counter torque device. The counter torque device helps to limit rotation to only those components necessary when rotating the tensioner driver. In some embodiments, the carriage 540 is capable of translation via the tensioner driver 550, thereby increasing the tension on the elastic member.

The tensioner driver 550 of the upper member 504 comprises a cylindrical member that is attached to a proximal end of the carriage 540. In some embodiments, the tensioner driver 550 can comprise a base portion that is received in a cut out portion of the carriage 540, thereby retaining the tensioner driver 550 to the carriage 540. The tensioner driver 550 includes internal threads that are configured to engage external threads of the threaded shaft 580. Rotation of the tensioner driver 550 in a first direction causes the tensioner driver 550 to rotate upwardly along the threaded shaft 580. As the tensioner driver 550 is attached to the carriage 540, the carriage 540 also translates upwardly, thereby increasing tension on the elastic member attached to the carriage 540. Rotation of the tensioner driver 550 in a second direction causes the tensioner driver 550 to rotate downwardly along the threaded shaft 580. This causes the carriage 540 to translate downwardly, thereby reducing tension on the elastic member attached to the carriage 540. In some embodiments, the tensioner driver 550 comprises a hex knob.

The threaded shaft 580 of the upper member 504 comprises external threads that engage internal threads of the tensioner driver 550. In some embodiments, the threaded shaft 580 comprises a proximal cap 584. Advantageously, the proximal cap 584 serves as a stop that prevents the tensioner driver 550 from going past the cap, thereby reducing the risk of the tensioner driver 550 from falling off the threaded shaft 580.

The method of using the instrument 500 is as follows. In some embodiments, the lower member 502 is delivered to receive a clamp 10, which can further receive a rod member 80 therein. An elastic member or band that extends through the clamp 10 can be pulled through a side opening or slot 531 of the bottom cam lock 530, thereby placing the elastic member in tension. The upper member 504 can then be delivered into attachment with the lower member 502, whereby it can be attached via a quick connection (e.g., a snap fit). The elastic member can then be pulled through a side opening or slot 561 of the top cam lock 560, whereby it can be retained in further tension. To increase tension on the elastic member, the tensioner driver 550 can be rotated, thereby causing upward translation of the carriage 540 upon which the top cam lock 560 resides. As the carriage 540 is drawn upwardly, this increases the tension on the elastic member. When the elastic member has achieved its desired tension, a set screw 25 (shown in FIG. 1A) can be downwardly threaded onto the elastic member, thereby securing the clamp 10 to bone. The instrument 500 can then be removed from the clamp. First, the upper member 504 can be released from the lower member 502 by pressing the release button 544. Second, the lower member 502 can be released from the clamp 10 by pushing the sleeve release button 544 of the sleeve 520 and drawing the sleeve 520 upwardly. This causes the fingers 512 to open, which thereby allows the clamp 10 to disengage from the instrument 500 if desired. In some embodiments, loose ends of the elastic member can be cut while attached to the instrument 500. In other embodiments, loose ends of the elastic member are cut after detachment of the instrument 500 from the elastic member. Any remaining loose ends of the elastic member can be glued, singed, or further cut if desired. At this time, the clamp 10 is securely retained on a bone member.

Figure 19:
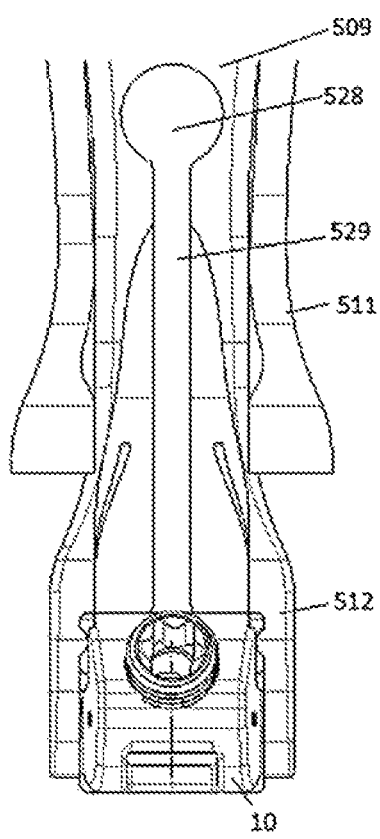
FIG. 19 is a close-up view of a lower member of the integrated holder and tensioner instrument of FIG. 18.

FIG. 19 is a close-up view of a lower member of the integrated holder and tensioner instrument of FIG. 12. From this view, one can see the shaft 509, as well as the rounded flex cut 528 and elongated flex cut 529 formed therein. The flex cuts 528, 529 advantageously help the instrument to retain a clamp 10, simply by downward force onto the clamp 10.

Figure 20:
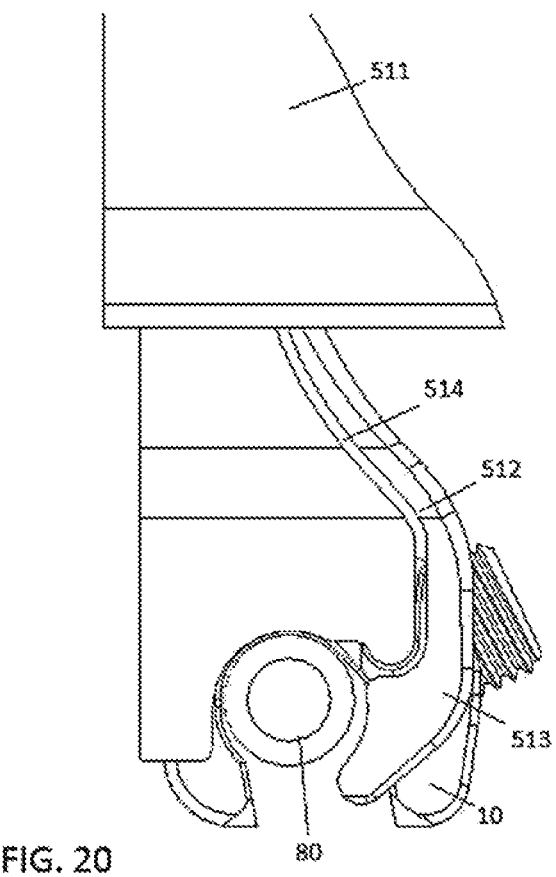
FIG. 20 is a side view of a lower member of the integrated holder and tensioner instrument of FIG. 18.

FIG. 20 is a side view of a lower member of the integrated holder and tensioner instrument of FIG. 18. From this view, one can see the fingers 512 in a "open" configuration, whereby a rod member 80 can be received therein. The fingers 512 include at least one hinged portion 513, whereby in the open configuration, the hinged portion 513 is away from the opposing finger, thereby providing room to receive the rod member 80. To maintain the fingers 512 in the open configuration, the sleeve 520 is pulled upwardly after pushing on the sleeve release button 517.

Figure 21:
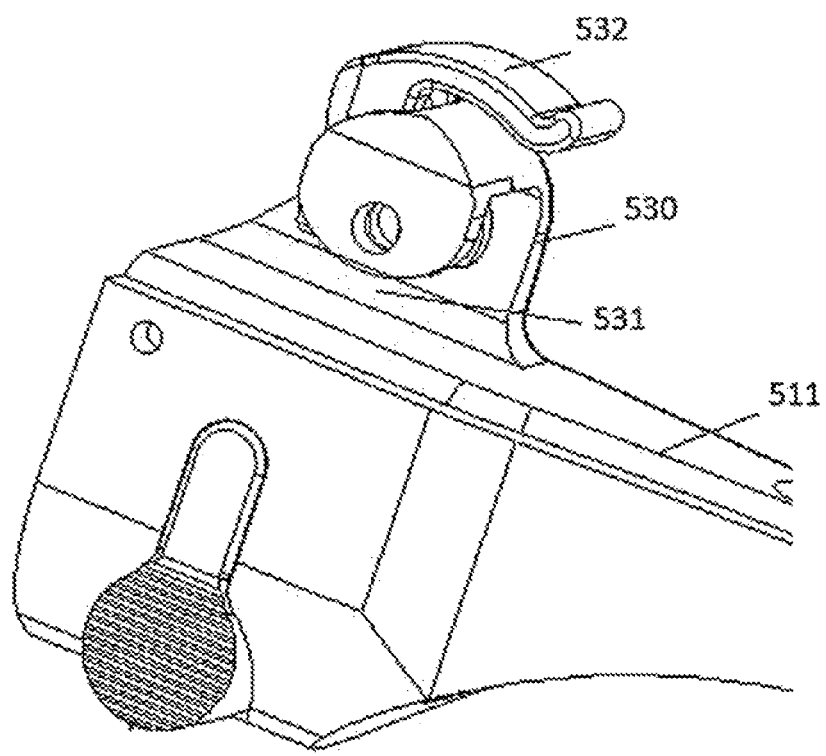
FIG. 21 is a side view of a lower member of the integrated holder and tensioner instrument of FIG. 18.

FIG. 21 a side perspective view of a lower member of the integrated holder and tensioner instrument of FIG. 18. From this view, one can see the bottom cam lock 530 close up. The bottom cam lock 530 includes a side-loaded opening or slot 531 for easily delivering an elastic member therein.

Figure 22:
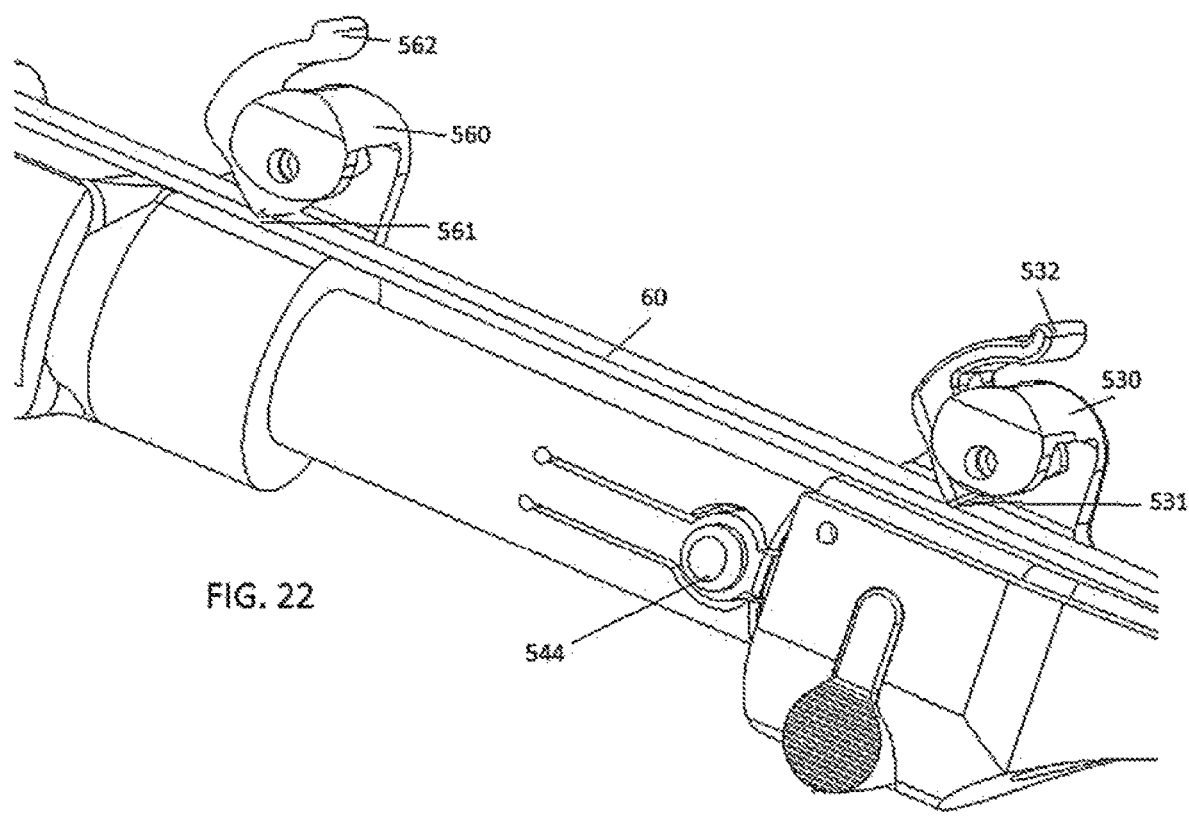
FIG. 22 is a perspective view of cam locks of the integrated holder and tensioner instrument of FIG. 18.

FIG. 22 is a perspective view of cam locks of the integrated holder and tensioner instrument of FIG. 18. From this view, one can see the bottom cam lock 530, the top cam lock 560 and the elastic member 60 that extends between the two cam locks. Advantageously, the elastic member 60 is side-loaded into each of the bottom cam lock 530 and the top cam lock 560, thereby making it easier to retain the elastic member 60 therein.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A surgical system comprising:
   an elastic member;
   a clamp for receiving the elastic member therein; and
   an instrument configured to hold the clamp and tension the elastic member, wherein the instrument comprises a lower member and a detachable upper member,
   wherein the lower member includes a sleeve configured to extend over a shaft, the lower member further configured to place fingers position on a distal end of the instrument in a closed configuration in a first position and in an open configuration in a second position,
   wherein the lower member of the instrument comprises a bottom cam lock having a side slot for receiving the elastic member therein, and,
   wherein the upper member comprises a top cam lock in line with the bottom cam lock for receiving the elastic member therein.

2. The system of claim 1, wherein the clamp further comprises a first opening and a second opening, wherein a set screw is received in the first opening.

3. The system of claim 2, wherein the elastic member is received in the second opening.

4. The system of claim 1, wherein the clamp further comprises an inner opening formed by an inner curved wall of the clamp, wherein the inner curved wall includes a groove for receiving the elastic member.

5. The system of claim 1, wherein the instrument further comprises a carriage operably attached to the tensioner driver.

6. A surgical system comprising:
   an elastic member;
   a clamp for receiving the elastic member therein; and
   an instrument configured to hold the clamp, wherein the instrument comprises an upper member, a lower member, and a sleeve, wherein the upper member comprises a top cam lock having a side slot for receiving the elastic member and the lower member comprises a bottom cam lock having a side slot for receiving the elastic member therein,
   wherein the lower member has a sleeve release button that allows the sleeve to move along a longitudinal path over a shaft.

7. The system of claim 6, wherein the clamp further comprises a set screw.

8. The system of claim 6, wherein the lower member of the instrument further comprises a clamp holder having fingers for holding the clamp.

9. The system of claim 6, wherein the instrument is configured to apply tension to the elongate member while holding the clamp.

10. The system of claim 9, wherein the instrument comprises a tensioner driver for applying tension to the elastic member.

11. The system of claim 10, wherein the tensioner driver is operably connected to a carriage, wherein the top cam lock extends from the carriage.

12. The system of claim 6, wherein the instrument further comprises a hex knob tensioner driver for increasing or decreasing tension on the elastic member.

13. A surgical system comprising:
   an elastic member;
   a clamp for receiving a rod member and the elastic member; and
   an instrument configured to hold the clamp, wherein the instrument comprises an upper member and a lower member, wherein the upper member is detachable from the lower member, wherein the lower member comprises a bottom cam lock for receiving the elastic member and the upper member comprises a top cam lock for receiving the elastic member, and
   wherein the lower member includes a sleeve configured to extend over a shaft, the lower member further configured to place fingers position on a distal end of the instrument in a closed configuration in a first position and in an open configuration in a second position.

14. The system of claim 13, wherein the elastic member is side-loaded into each of the bottom cam lock and the top cam lock.

15. The system of claim 14, wherein the bottom cam lock comprises a release latch.

16. The system of claim 13, wherein the instrument further comprises a tensioner driver and a carriage.

17. The system of claim 16, wherein the top cam lock extends from the carriage, wherein rotation of the tensioner driver causes the carriage to translate such that tension increases on the elastic member.

18. The system of claim 17, wherein the tensioner driver is a hex knob tensioner driver.

* * * * *